(12) United States Patent
Kerns

(10) Patent No.: US 10,384,020 B2
(45) Date of Patent: *Aug. 20, 2019

(54) INFANT EPINEPHRINE AUTOINJECTOR

(71) Applicant: University Hospitals Case Medical Center, Cleveland, OH (US)

(72) Inventor: Leigh Ann Kerns, Mayfield, OH (US)

(73) Assignee: UNIVERSITY HOSPITALS CASE MEDICAL CENTER, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/827,866

(22) Filed: Nov. 30, 2017

(65) Prior Publication Data
US 2018/0085535 A1 Mar. 29, 2018

Related U.S. Application Data

(63) Continuation of application No. 14/921,916, filed on Oct. 23, 2015, now Pat. No. 9,861,765.

(60) Provisional application No. 62/068,063, filed on Oct. 24, 2014.

(51) Int. Cl.
| | | |
|---|---|---|
| *A61M 31/00* | (2006.01) | |
| *A61M 5/00* | (2006.01) | |
| *A61M 5/46* | (2006.01) | |
| *A61M 5/20* | (2006.01) | |
| *A61M 5/28* | (2006.01) | |
| *A61M 5/32* | (2006.01) | |

(52) U.S. Cl.
CPC ............ *A61M 5/46* (2013.01); *A61M 5/2033* (2013.01); *A61M 5/283* (2013.01); *A61M 5/326* (2013.01); *A61M 2005/206* (2013.01); *A61M 2005/2013* (2013.01); *A61M 2205/19* (2013.01); *A61M 2240/00* (2013.01)

(58) Field of Classification Search
CPC .......... A61M 2205/19; A61M 2240/00; A61M 5/46; A61M 2005/2013; A61M 2005/206; A61M 5/2033; A61M 5/283; A61M 5/31576; A61M 5/31578; A61M 5/3221; A61M 5/326
USPC ........................................................ 604/506
See application file for complete search history.

(56) References Cited

U.S. PATENT DOCUMENTS

2005/0171477 A1* 8/2005 Rubin ................. A61M 5/2033
604/156

OTHER PUBLICATIONS

Stecher et al., "Epinephrine Auto-Injectors: Is Needle Length Adequate for Delivery of Epinephrine Intramuscularly?", Pediatrics Official Journal of the American Academy of Pediatrics, vol. 124, No. 1, Jul. 2009, p. 65-70.

* cited by examiner

*Primary Examiner* — Jason E Flick
(74) *Attorney, Agent, or Firm* — Fay Sharpe LLP

(57) ABSTRACT

An injection device suitable for use with infants is disclosed. The injection device is formed from a body shield member and a cylindrical handle. The body shield member includes a concave flange at the base, which is pressed against the patient's limb and reduces local compression at the needle insertion site. The injection device also has a softer form and operates through a pressing motion. A catch member is located in the cylindrical handle, and is deployed upon fully depressing the handle. Once the handle returns to its starting position, the catch member prevents the handle from being depressed a second time and permitting the used needle to be exposed.

20 Claims, 30 Drawing Sheets

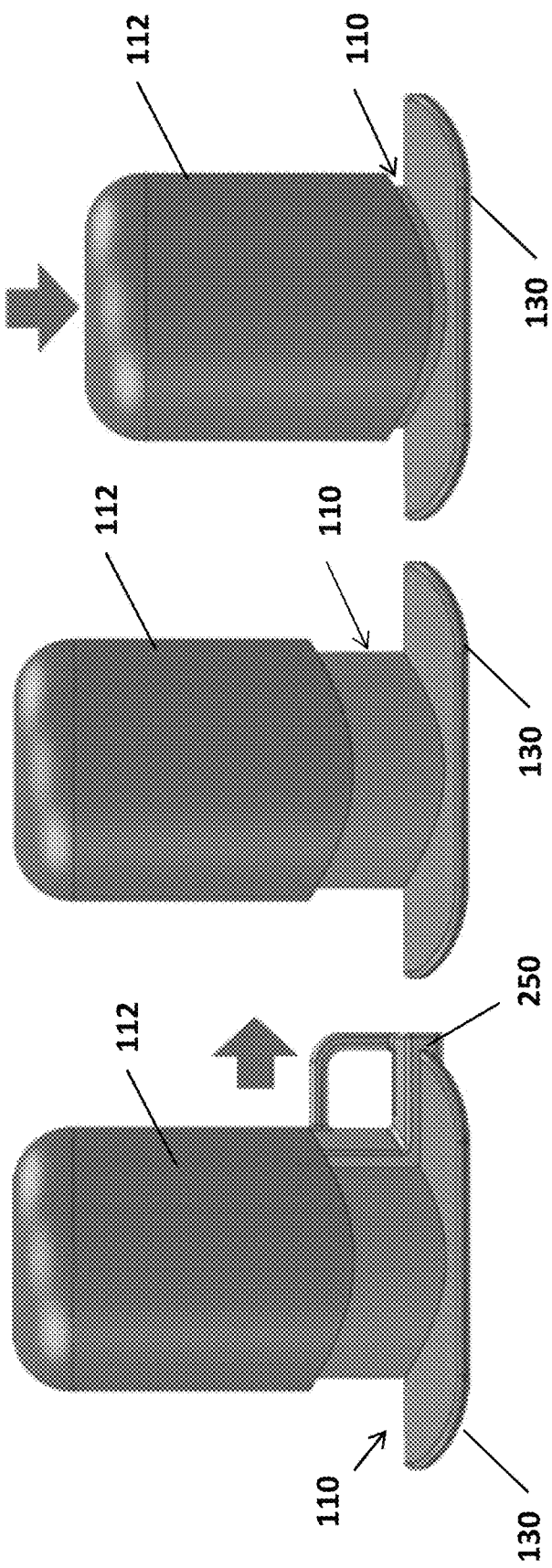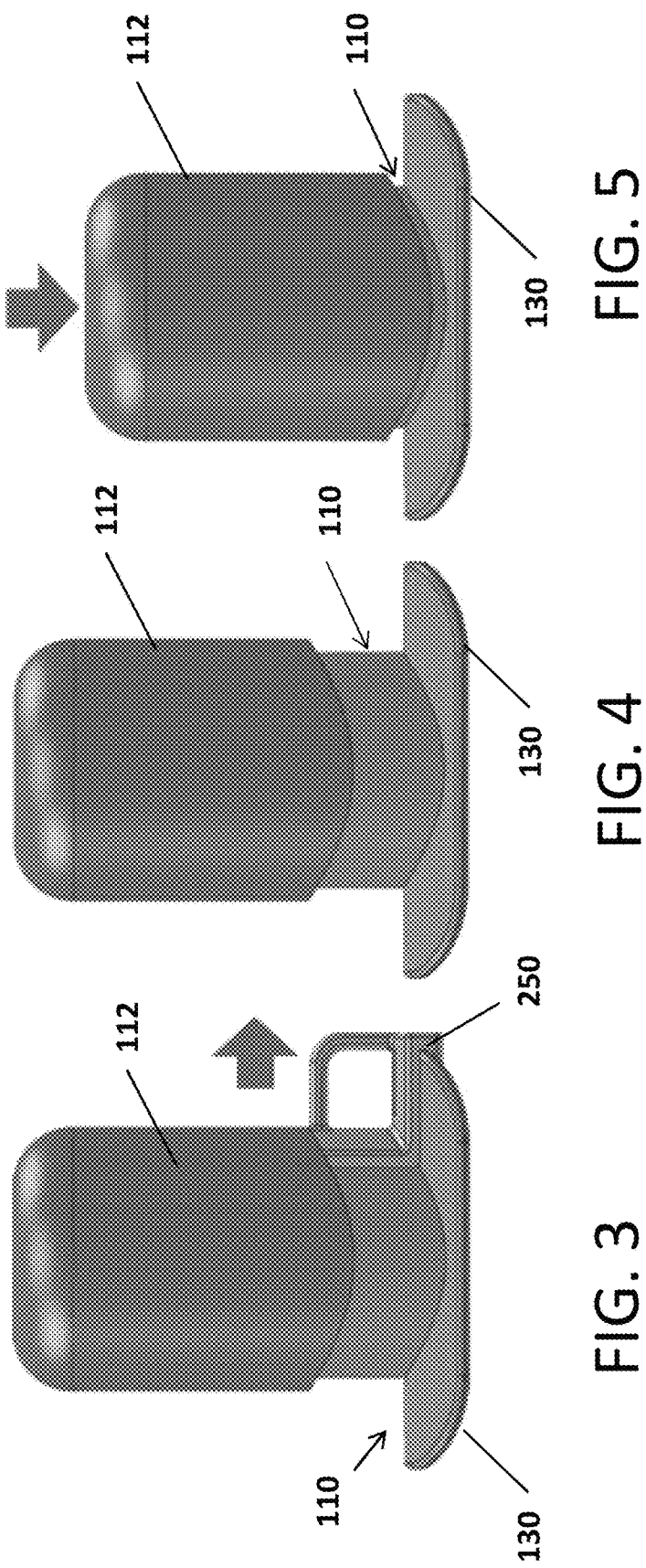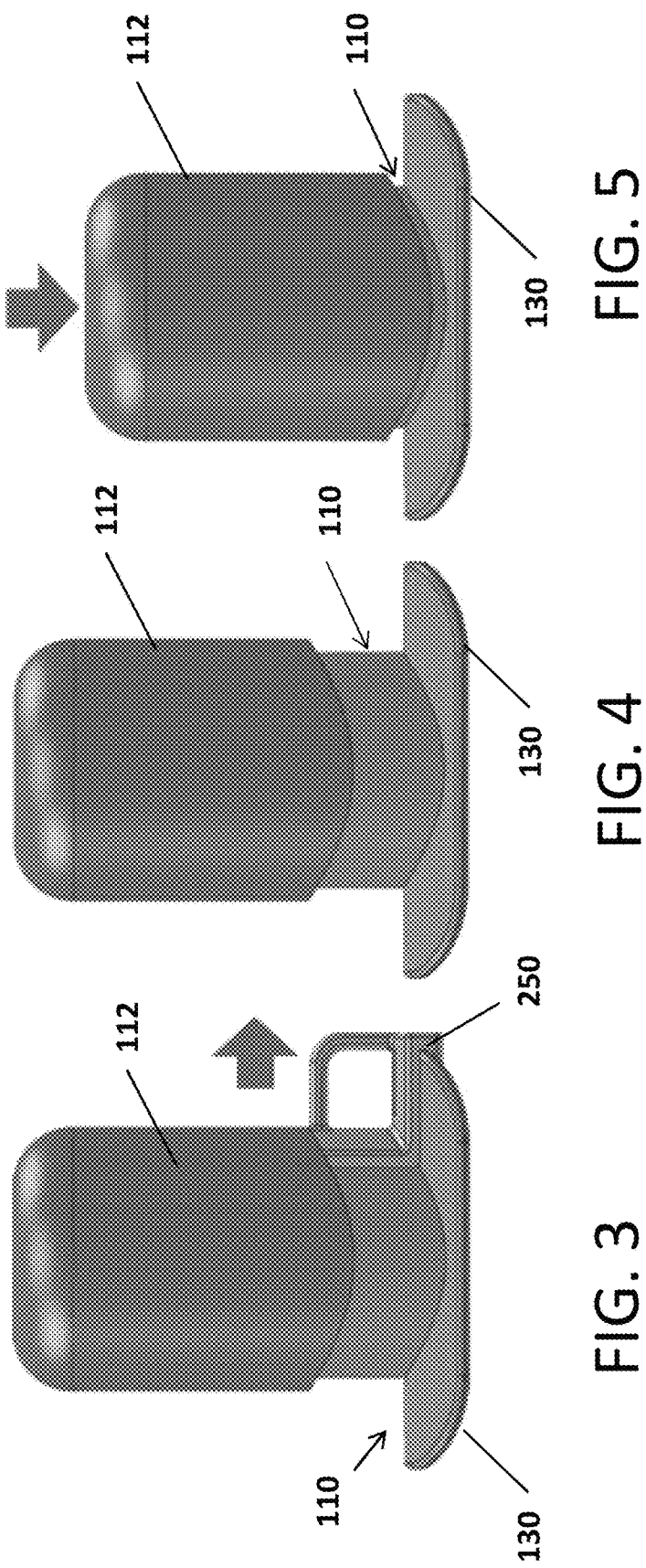

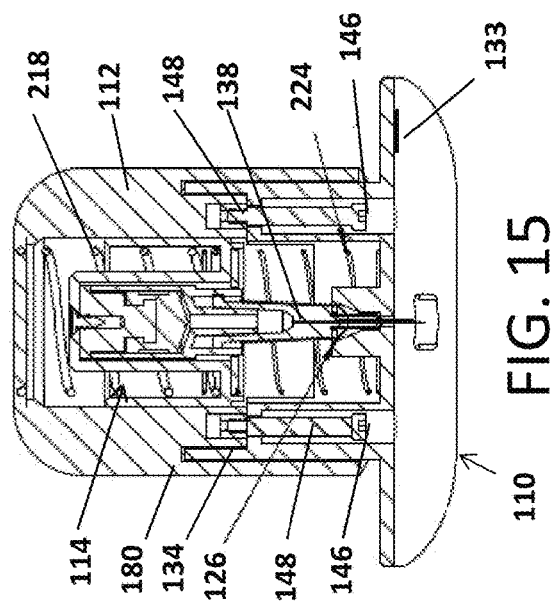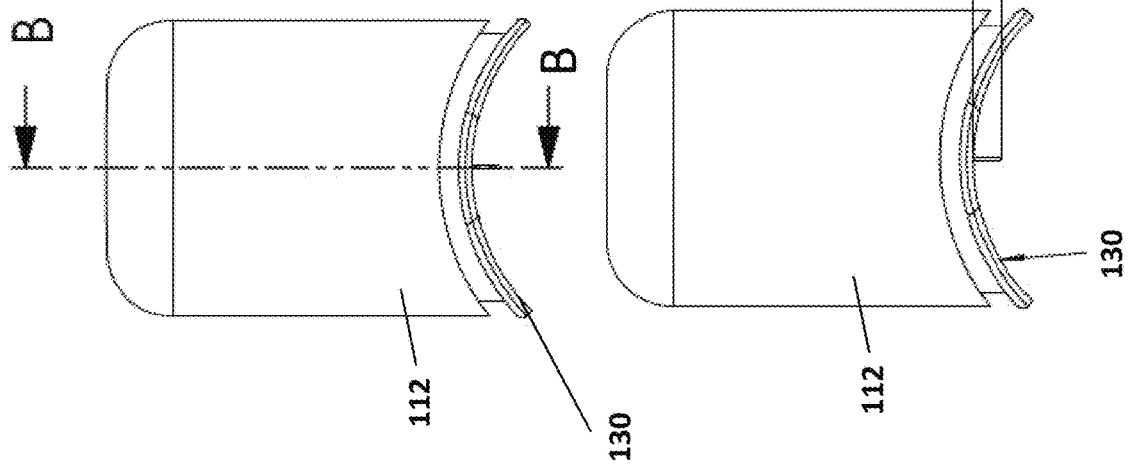

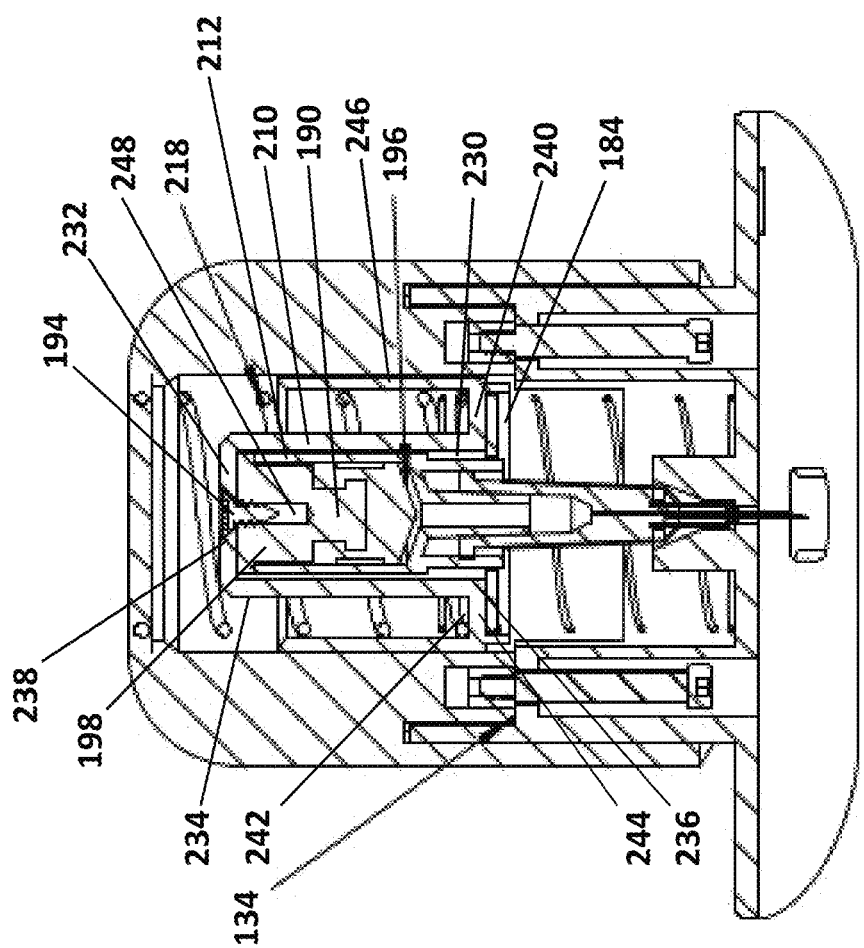

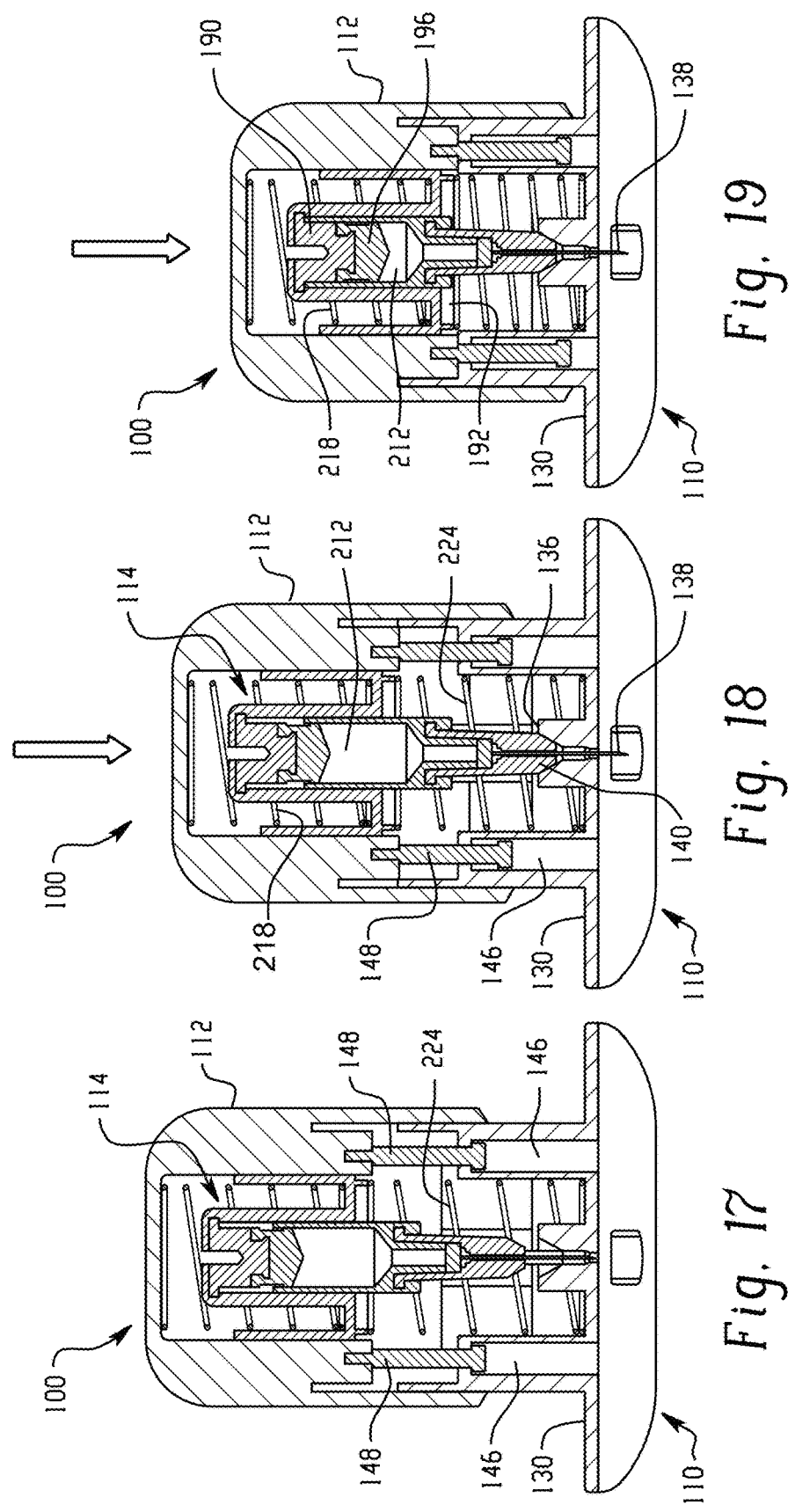

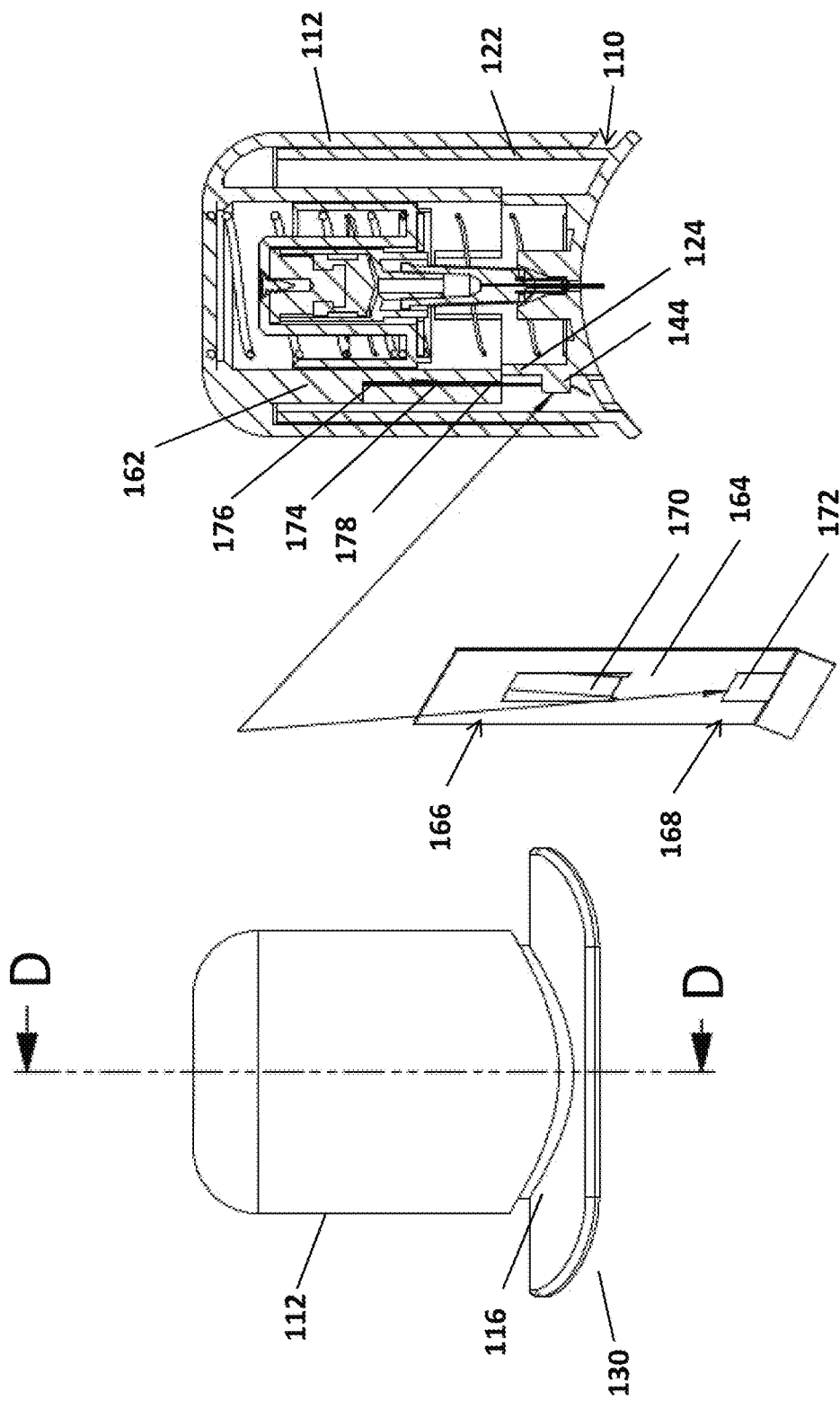

INFANT EPINEPHRINE AUTOINJECTOR

CROSS-REFERENCE TO RELATED APPLICATIONS

This application is a continuation of U.S. patent application Ser. No. 14/921,916, filed Oct. 23, 2015, now U.S. Pat. No. 9,861,765, which claims priority to U.S. Provisional Application Ser. No. 62/068,063, filed Oct. 24, 2014, which is expressly incorporated herein by reference.

BACKGROUND

The present disclosure relates to injection devices that are modified to be more user-friendly and that operate in a non-threatening manner. In particular, such devices are autoinjecting devices that are designed for use with infants of less than 10 kg in size. The devices have design features intended to simplify administration and to control the penetration depth of the needle.

Several medications are commonly administered via auto-injection devices by parents or caregivers. For example, insulin is administered for the treatment of diabetes. Another common medication administered by parents or caregivers includes epinephrine for treating severe allergic reactions. Food allergies are increasing in prevalence, and about 5% of children under three years of age have a food allergy. Epinephrine is the only treatment for severe allergic reactions.

Epinephrine auto-injectors are designed to be administered by non-medical personnel to treat severe reactions. A prior art device is illustrated in FIG. 1. As seen here, the device is shaped like a needle or a knife, which can be visually threatening. The device is used by "stabbing" the patient, which can be intimidating both to the patient and to the person using the device. The device uses a spring to deploy and inject, and the action of the spring can be very loud. The stabbing motion also provides less control of the device. In addition, the needle penetration depth will change depending on the pressure applied in the stabbing motion. The pressure can also cause the tissue at the injection site to be compressed. This combination of features can cause possible injury to the patient.

Epinephrine auto-injectors are currently available in two sizes. The first size contains a 0.3 mg dose (ideal for a 30 kg patient) with a five-eighths-inch (⅝", 1.58 cm) needle length. The second size contains a 0.15 mg dose (ideal for 15 kg patient) with a half-inch (½", 1.27 cm) needle length. These epinephrine auto-injectors contain a dose that is too high for infants, especially those with weight of less than 10 kg. Also, the needle lengths of these needles may be too long to ensure intramuscular injection in an infant.

It would be desirable to provide autoinjection devices that can provide a dose more appropriate for infants <10 kg and a shorter needle. Such a design also desirably makes it easier for parents to administer the medication to infants.

BRIEF DESCRIPTION

The present disclosure relates to autoinjection devices that operate differently from those of the prior art. The devices of the present disclosure have a softer form language. They operate somewhat like a button, with a pressing motion, instead of a stabbing motion. The device is first placed against the patient's limb and then depressed, permitting finer control over the injection location. The device also includes a flange shaped like the patient's limb, which acts as a shield. This increases the surface area over which pressure is applied, better controlling any tissue depression and making injury less likely. The action is also softer and quieter.

Disclosed in various embodiments are injectors for delivering a dose of a pharmaceutical, comprising: (a) a body shield member for engaging a limb; (b) a cylindrical handle; and (c) a syringe assembly. The body shield member comprises: a central pipe portion formed from an outer sidewall that defines an upper end and a lower end of the body shield member: a concave flange on the lower end of the body shield member; an orifice located at the lower end along a central axis through which a needle is exposed; a stop wall surrounding the orifice and having a top surface which controls the exposure depth of the needle; and an inner sidewall located within the central pipe portion and surrounding the stop wall. The cylindrical handle travels along the central axis relative to the central pipe portion of the body shield member, and comprises: a handle sidewall that defines an upper end and a lower end of the cylindrical handle, the handle sidewall surrounding the central pipe portion of the body shield member; a top circular plane surface on the upper end of the handle; and an internal cavity defined by a cavity wall that extends from the upper end to the lower end of the handle. The syringe assembly has an upper end and a lower end, the upper end being disposed within the internal cavity of the handle against the top circular plane surface, the lower end disposed within the inner sidewall of the body shield member. The syringe assembly comprises: a plunger assembly having a push disc and a head; a syringe barrel having an upper end and a lower end, the upper end slidably receiving the plunger head, the lower end being attached to the needle; a high-force compression spring having an upper end and a lower end, the upper end engaging the upper end of the handle, the lower end acting on the push disc of the plunger assembly; and a low-force compression spring having an upper end and a lower end, the upper end acting on the syringe barrel, the lower end being located within the inner sidewall of the body shield member and on a top surface of the concave flange. When the handle is in a start position, the low-force compression spring biases the handle apart from the body shield member. When the handle is in a partially depressed position, the lower end of the syringe assembly engages the stop wall of the body shield member, and the needle is exposed below the concave flange. When the handle is in the fully depressed position, the plunger head has traveled through the syringe barrel.

In some further embodiments, (a) the body shield member further comprises a boss on an outer surface of the inner sidewall, the boss extending away from the central axis; and (b) the cylindrical handle further comprises: a catch member having an upper end and a lower end, a bent arm at the upper end which extends upward, and a hole at the lower end for engaging the boss on the inner sidewall of the body shield member; and a slot in the cavity wall. When the handle is in a start position, the upper end of the catch member is housed within the slot, the hole in the catch member remaining exposed. When the handle is in the fully depressed position, the hole of the catch member engages the boss of the body shield member. As the handle moves back to the start position, the upper end of the catch member is pulled out of the slot due to the engagement of the hole with the boss, causing the bent arm to engage a bottom surface of the cavity wall and prevent the handle from being depressed again.

The plunger assembly can be formed from a syringe slide and a plunger stem. The syringe slide may comprise a hollow center body having a top wall and an open bottom, an annulet surrounding the open bottom that has a top surface and a bottom surface, and a sidewall extending upward from an outside diameter of the annulet. An upper end of the plunger stem is fixed in place within the hollow center body of the syringe slide, and the plunger head is located at a lower end of the plunger stem. The lower end of the high-force compression spring engages the top surface of the annulet, which acts as the push disc of the plunger assembly.

In particular embodiments, the body shield member may further comprise an engagement feature on the upper end of the outer sidewall, the cylindrical handle further comprises a mating feature, and the engagement feature engages the mating feature when the handle is in the fully depressed position.

The upper end of the low-force compression spring may engage the lower end of the syringe barrel. The upper end of the low-force compression spring can contact a retention disc that acts against the lower end of the syringe barrel.

The injector may further comprise a safety pull which prevents the handle sidewall of the cylindrical handle from moving towards the concave flange of the body shield member when the safety pull engages the body shield member. The safety pull may comprise a cover surface for covering the orifice of the body shield member when the safety pull engages the body shield member.

The perimeter of the top circular plane surface of the injector can be chamfered.

In certain embodiments, the body shield member has at least one bore, the cylindrical handle has at least one socket, and a fastener passes through the at least one bore of the body shield member to engage the at least one socket, the fastener preventing the handle from separating from the body shield member.

The high force spring may require approximately 150 grams to compress. The low-force spring may require approximately 50 grams to compress. The syringe barrel may have a volume of approximately 0.3 cc. The needle may be a 30 gauge needle.

Also disclosed in various embodiments are other injectors for delivering a dose of a pharmaceutical, comprising: (a) a body shield member for engaging a limb; (b) a cylindrical handle; and (c) a syringe assembly.

The body shield member comprises: a central pipe portion formed from an outer sidewall that defines an upper end and a lower end of the body shield member: a concave flange on the lower end of the body shield member; an orifice located at the lower end along a central axis through which a needle is exposed; a stop wall surrounding the orifice and having a top surface which controls the exposure depth of the needle; and an inner sidewall located within the central pipe portion and surrounding the stop wall. The cylindrical handle travels along the central axis relative to the central pipe portion of the body shield member, and comprises: a handle sidewall that defines an upper end and a lower end of the cylindrical handle, the handle sidewall surrounding the central pipe portion of the body shield member; a top circular plane surface on the upper end of the handle; an internal cavity defined by a cavity wall, extending from the upper end to the lower end of the handle; and a boss on an interior surface of the handle sidewall at an upper end of the handle. The syringe assembly has an upper end and a lower end, the upper end being disposed within the internal cavity of the handle against the top circular plane surface, the lower end disposed within the inner sidewall of the body shield member. The syringe assembly comprises: an inner barrel with a push wall and a sidewall, the sidewall having at least one pin extending outward from the sidewall; an outer sleeve surrounding the inner barrel, the outer sleeve having a sidewall including a helically curved slot mating with the at least one pin of the inner barrel, and having a flange on a lower end of the sleeve extending outward from the sidewall; a plunger assembly having a push disc and a head; a syringe barrel having an upper end and a lower end, the upper end slidably receiving the plunger head, the lower end being attached to the needle; a torsion spring surrounding the outer sleeve and having an upper end and a lower end, the upper end engaging the handle boss, the lower end engaging the flange of the outer sleeve; and a low-force compression spring having an upper end and a lower end, the upper end acting on a bottom surface of the inner barrel, the lower end being located within the inner sidewall of the body shield member and on a top surface of the concave flange. When the handle is in a start position, the low-force compression spring biases the syringe assembly apart from the body shield. When the handle is in a partially depressed position, the lower end of the syringe assembly engages the stop wall of the body shield member, and the needle is exposed below the concave flange. When the handle is in a fully depressed position, the plunger head has traveled through the syringe barrel. As the handle moves back to the start position, the needle is retracted into the orifice.

The body shield member may include a ridge to maintain a minimum distance between the outer sleeve and the concave flange. The body shield member can include a retainer that surrounds the outer sleeve and attaches to the cylindrical handle, the retainer being used to maintain a minimum distance between the outer sleeve and the concave flange.

The inner barrel may have a barbell shape, and the cylindrical handle may include two rails along which the inner barrel travels.

Also disclosed herein are methods of delivering a dose of a pharmaceutical through an injector, comprising: providing an injector formed from a body shield member capable of preventing local compression of the skin on a patient's limb, a press handle, and a syringe assembly; placing the body shield member against the patient's limb; pressing the handle toward the limb, causing the syringe assembly to extend a needle for a specified penetration depth; injecting a specified dosage into the patient for a predetermined period of time; retracting the needle into the injector after a predetermined period of time; locking the handle so that it cannot be pressed again and the needle cannot be re-exposed; and removing the injector from the patient's limb.

Some embodiments of these methods further comprise removing a safety pull allowing the press handle to be pressed. The specified penetration depth may correspond to a needle length of less than one-half inch. The predetermined period of time for injecting a specified dosage may be about 3 seconds. The specified dosage may be about 0.3 cc of the pharmaceutical.

These and other non-limiting aspects and/or objects of the disclosure are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 3 is a front view showing an injection device of the present disclosure in its start position and being prevented from moving from its start position via a safety pull.

FIG. 4 is a front view showing the injection device of the present disclosure in its start position, with the safety pull removed.

FIG. 5 is a front view showing the injection device of the present disclosure in its fully depressed or deployed position.

FIG. 13 is an exterior side view of the first exemplary embodiment in a fully-depressed position, and shows the needle extending from the bottom of the device, i.e. beyond the concave flange.

FIG. 14 is a second exterior side view of the first exemplary embodiment in a fully-depressed position, and shows the line BB.

FIG. 15 is a front cross-sectional view taken along the line BB of FIG. 14, and shows some aspects of the internal mechanisms in the injector.

FIG. 16 is the same cross-sectional view as FIG. 15, but with additional reference numerals describing the syringe slide and the plunger.

FIG. 17 is a front cross-sectional view showing the first exemplary embodiment of an injection device of the present disclosure in its start position.

FIG. 18 is a front cross-sectional view showing the first exemplary embodiment of an injection device of the present disclosure in its partially-depressed position.

FIG. 19 is a front cross-sectional view showing the first exemplary embodiment of an injection device of the present disclosure in its fully-depressed position.

FIG. 20 is a front exterior view showing the first exemplary embodiment of an injection device of the present disclosure in its fully-depressed position.

FIG. 21 is a side cross-sectional view taken along the line DD of FIG. 20 showing various aspects of a locking mechanism for the first exemplary embodiment of an injection device of the present disclosure.

FIG. 22 is a perspective view of a catch member used in the locking mechanism.

DETAILED DESCRIPTION

Figure 2:
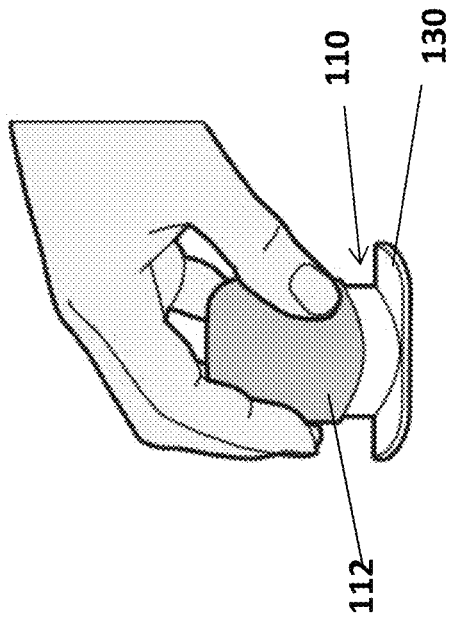
FIG. 2 is an illustration showing an injector of the present disclosure and how the injector would be held by a user.

A more complete understanding of the devices and methods disclosed herein can be obtained by reference to the accompanying drawings. These figures are merely schematic representations based on convenience and the ease of demonstrating the existing art and/or the present development, and are, therefore, not intended to indicate relative size and dimensions of the assemblies or components thereof.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function. In the following specification and the claims which follow, reference will be made to a number of terms which shall be defined to have the following meanings.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named components/steps and permit the presence of other components/steps. However, such description should be construed as also describing devices or methods as "consisting of" and "consisting essentially of" the enumerated components/steps, which allows the presence of only the named components/steps, and excludes other components/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases.

All ranges disclosed herein are inclusive of the recited endpoint and independently combinable (for example, the range of "from 2 to 10" is inclusive of the endpoints, 2 and 10, and all the intermediate values).

The terms "upper" and "lower" are used to describe the orientation of different components relative to an axis of the device. The upper end of a first component and the upper end of a second component are both oriented in the same direction on the axis, as are their lower ends.

The present disclosure relates to autoinjection devices, also known as syringes, injectors, or auto-injectors. The injectors have a concave flange that rests on the patient's limb, an ergonomic shape, and are operated using a pressing motion along an axis generally normal to the patient's limb. It is contemplated that these devices will also be somewhat small in size, and are specifically contemplated for use with infants.

Figure 1:
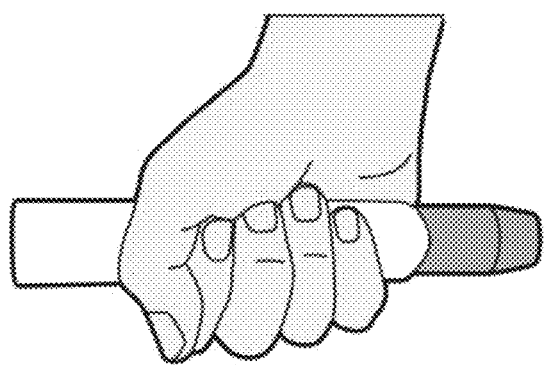
FIG. 1 is an illustration of an auto-injector known in the prior art.

FIG. 2 is a front view of the exterior of the injectors of the present disclosure, with a hand shown to illustrate how the injector is used. The exterior of the injector is formed from a body shield member 110 and a handle 112. The bottom end of the body shield member includes a concave flange 130. As illustrated here, it is contemplated that rather than being held and "stabbed" like the prior art device of FIG. 1, the device will be pressed like a button.

FIGS. 3-5 illustrate the use of the injector 100. In this regard, for one complete usage of the injector, the cylindrical handle 112 moves from a start position to a partially-depressed position, from the partially-depressed position to a fully-depressed position, and from the fully-depressed position back to the start position. The cylindrical handle 112 is then locked in the start position.

In FIG. 3, the injector 100 is shown with an optional safety pull 250 in place. As seen here, the safety pull prevents the handle 112 from moving towards the concave flange 130 of the body shield member 110, or in other words from being depressed. The safety pull 250 is removed from its engagement with the concave flange 130 in the direction indicated by the arrow. Once the safety pull 250 is clear of the concave flange 130, as illustrated in FIG. 4, the user may press down on the cylindrical handle in the direction of the arrow indicated in FIG. 5. FIG. 3 and FIG. 4 illustrate the start position, while FIG. 5 illustrates the fully-depressed position.

Figure 6:
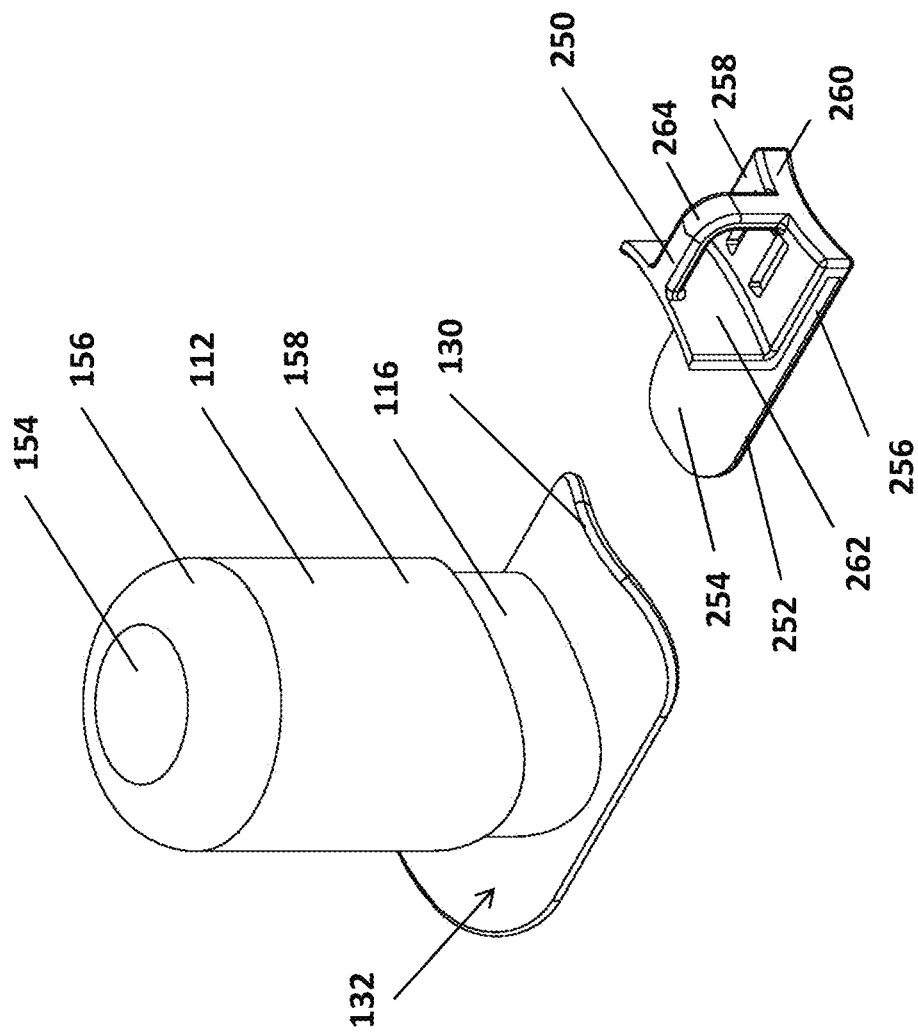
FIG. 6 is an exterior perspective view of an injection device of the present disclosure, with the safety pull removed.

FIG. 6 is a perspective view of the injection device 100 and the safety pull 250. The body shield member 130 has a top surface 132. A central pipe portion 116 extends upwards from the body shield member 130. The cylindrical handle 112 includes a top circular plane surface 154 and a handle sidewall 158. The top plane surface 154 is chamfered along its perimeter 156 where it joins the handle sidewall 158.

The safety pull 250 includes a concave lip 252 that extends under the concave flange 130 for a distance sufficient to cover an orifice on the bottom of the flange 130, from which the needle will protrude. The concave lip 252 thus acts to prevent accidental needle exposure prior to injector use. The top surface 254 of the concave lip 252 is cambered to match the camber of the concave flange 130. When the safety pull 250 is affixed to the injector, the top surface 254 slidably mates with the bottom of concave flange 130. The flange 130 extends into the recess 256 of the safety pull 250. The recess is bounded by a first curved sidewall portion 260, which extends upward from the end of the concave lip 252 at approximately a 90 degree angle. A concave recess wall 258 extends from the first curved sidewall portion over the concave flange 130. The concave recess wall is also cambered to match the concave flange 130. A second curved sidewall portion 262 then extends upwards from the other end of the concave recess wall 258 at approximately a 90 degree angle. The second curved sidewall portion 262 is received between the top surface 132 of the concave flange 130 and the bottom of the handle sidewall 158. The second curved sidewall portion 262 thus acts to prevent the cylindrical handle 112 from being accidentally depressed. A safety pull handle 264 extends between the second curved sidewall portion 262 and the first curved sidewall portion 260, and is bent to create a hole such that a user can easily grasp the safety pull 250 for removal.

Figure 7:
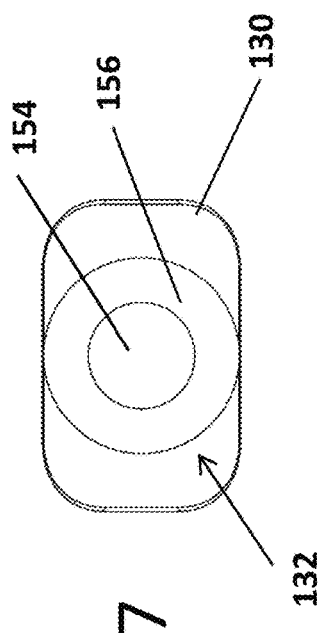
FIG. 7 is a top exterior view of an injection device of the present disclosure.

FIGS. 7-10 provide different views of the injection device. FIG. 7 is a top view. The top plane surface 154, the chamfered perimeter 156, and the top surface 132 of the concave flange 130 are visible.

Figure 8:
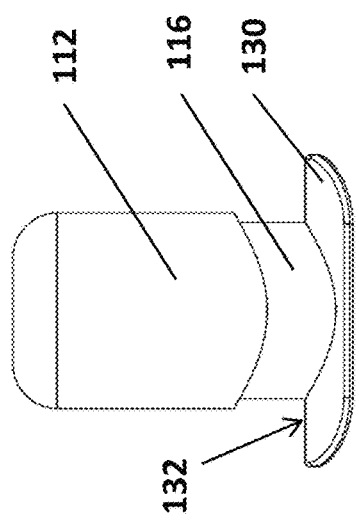
FIG. 8 is a front exterior view of an injection device of the present disclosure.

FIG. 8 is a front view. The concave flange 130, its top surface 132, and the central pipe portion 116 of the body shield member are visible. The cylindrical handle 112 is joined thereto. It is noted that the central pipe portion 116 is in the center of the concave flange 130.

Figure 9:
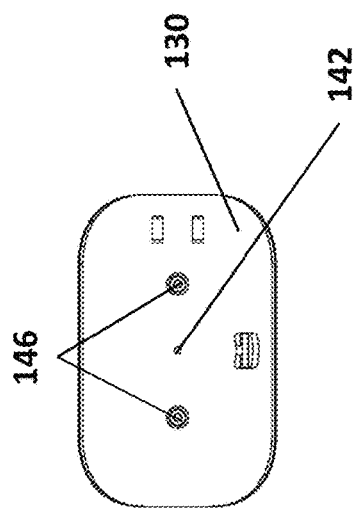
FIG. 9 is a bottom exterior view of an injection device of the present disclosure.

FIG. 9 is a bottom view. Visible on the bottom of the concave flange 130 is the orifice 142 from which the needle protrudes when the handle is fully depressed. Also visible are two bores 146. As will be explained later, the bores are used to join the body shield member and the cylindrical handle together so they cannot be easily separated.

Figure 10:
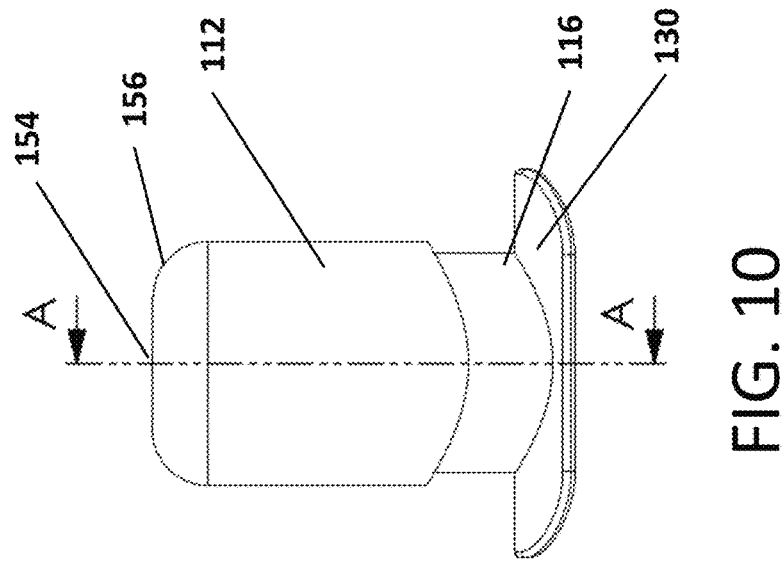
FIG. 10 is a rear exterior view of an injection device of the present disclosure, and is identical to the front exterior view of FIG. 8.

Finally, FIG. 10 is a rear view. The exterior of the injection device is rectangularly symmetrical, and appears the same from the front view (FIG. 8) or the rear. Besides the concave flange 130 and the central pipe portion 116, the top surface 154 and the chamfered perimeter 156 of the handle 112 are also labeled.

Figure 11:
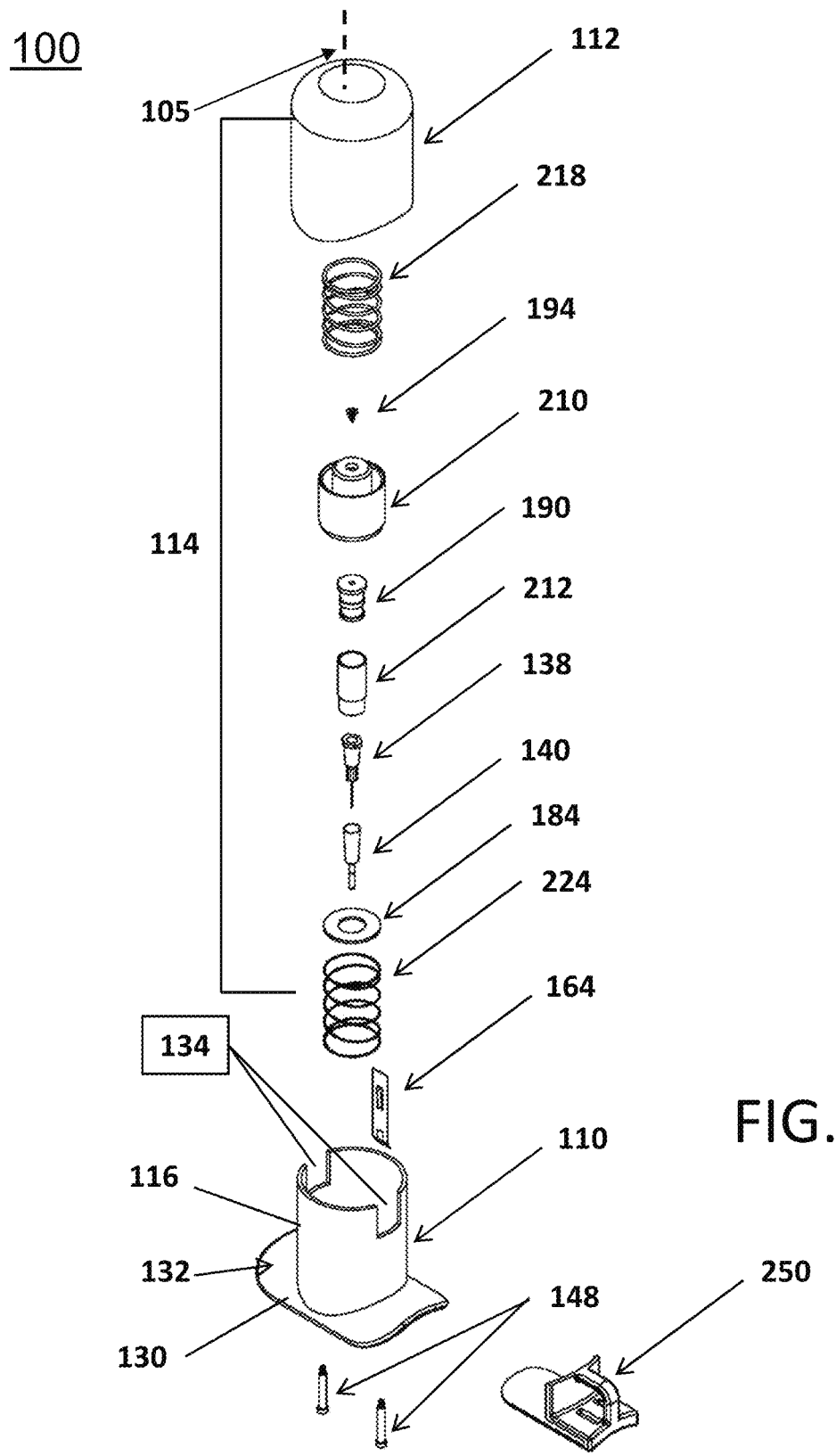
FIG. 11 is an exploded perspective view showing a first exemplary embodiment of an injection device of the present disclosure.

Two different embodiments of the injection devices of the present disclosure are described herein. An exploded view of the first exemplary embodiment is shown in FIG. 11. Generally, the injector 100 is comprised of three main components: a body shield member 110, a cylindrical handle 112, and a syringe assembly 114. The body shield member 110, cylindrical handle 112, and syringe assembly 114 are arranged vertically along a common central axis 105.

As seen in FIG. 11, the cylindrical handle 112 forms part of the exterior of the injector. The syringe assembly 114 is housed within the cylindrical handle 112 and the central pipe portion 116 of the body shield member 110. As illustrated here, the syringe assembly 114 is composed of a high-force compression spring 218, a screw 194 which fixes the syringe slide 210 to the plunger 190, a syringe barrel 212, a needle 138, an optional needle sheath 140, an optional retention disc 184, and a low-force compression spring 224. The optional needle sheath 140 which can be made of any suitable material for maintaining sterility of the needle, such as rubber and the like. The optional washer or retaining disc 184 is disposed between the syringe barrel 212 and the low-force compression 224. A catch member 164 is also located within the injector 100, and as explained further herein, is used to ensure the injector 100 can only be used once, or to ensure that the needle 138 cannot be deployed a second time.

The body shield member 110 is the other exterior member the injector 100. The body shield member includes a concave flange 130 with a top surface 132. Extending upward from the top surface 132 is a central pipe portion 116, which includes engagement features 134 for engaging the cylindrical handle 112. The body shield member 110 and the cylindrical handle 112 can be attached together via fasteners 148, which prevent these two main body parts from separating under the spring loads exerted by the high-force and low-force compression springs 218 and 224, respectively. The safety pull 250 is optional, but is shown here again.

Figure 12:
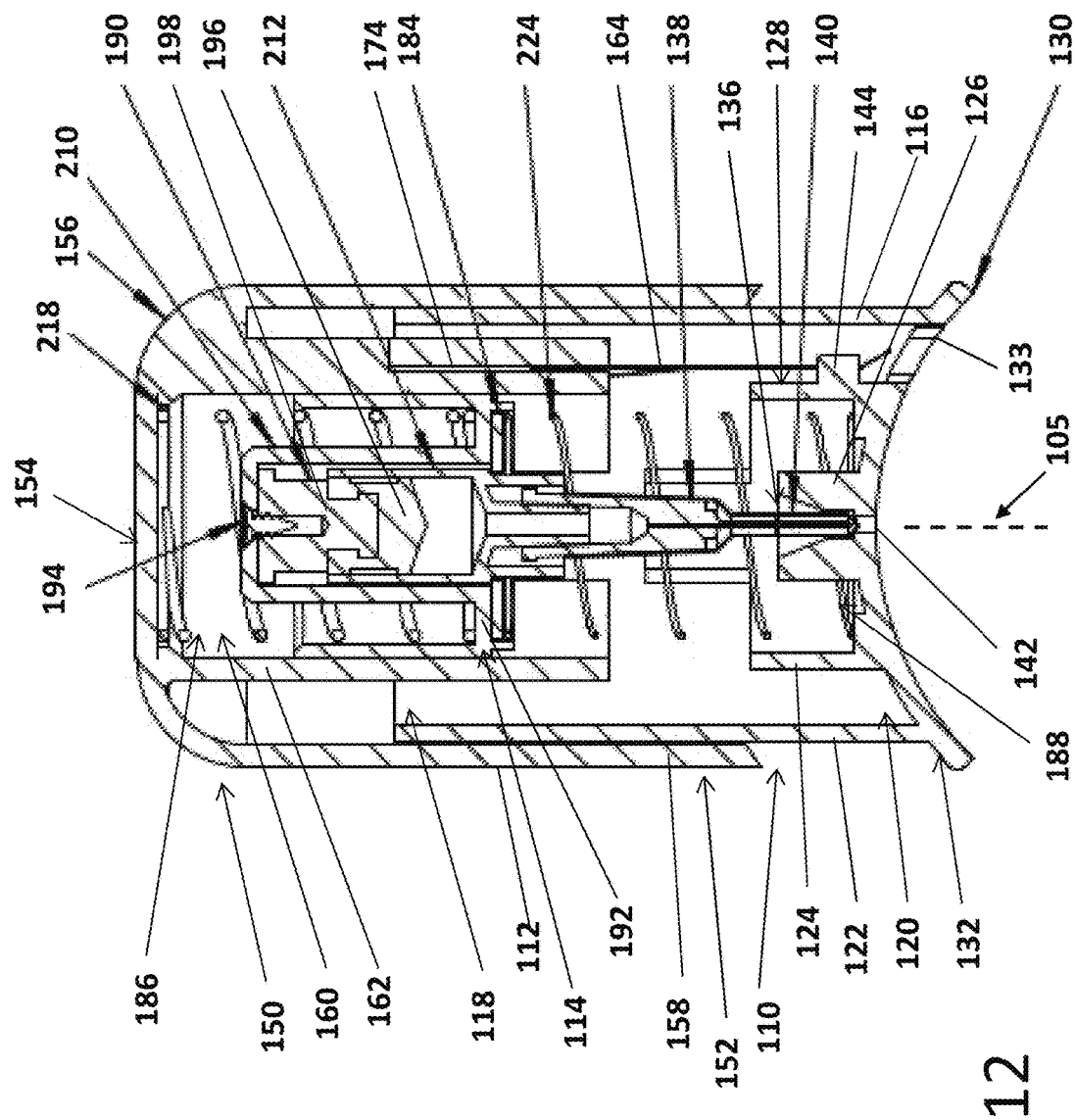
FIG. 12 is a cross-sectional view taken along the line AA of FIG. 10, and shows the first exemplary embodiment of an injection device of the present disclosure.

FIG. 12 is a cross-sectional side view of the first exemplary embodiment, taken with respect to line AA in FIG. 10. The body shield member 110 is the portion of the injector which comes into contact with the patient. The body shield member 110 has a central pipe portion 116 formed from an outer sidewall 122. The outer sidewall 122 defines an upper end 118 and a lower end 120 of the central pipe portion 116 and the body shield member. Disposed within the outer sidewall 122 of the central pipe portion 116 is a concentric inner sidewall 124, which has an outer surface 128. The inner sidewall is relatively shorter in height compared to the outer sidewall 122. A boss 144 extends transversely from the outer surface 128 of the inner sidewall 124, in the direction away from the central axis indicated by dashed line 105. Disposed within the inner sidewall is a stop wall 126. The stop wall 126 has a stop surface 136 and surrounds the orifice 142. The stop wall 126 will engage the needle 138 to control the length of the needle that is exposed beyond the orifice. A needle sheath 140 surrounds the needle. The orifice 142 extends through a concave flange 130, permitting the needle to pass from one side to the other.

The concave flange 130 is located at the lower end 118 of the body shield member 110. The concave flange 130 extends outwardly from both sides of the central pipe portion 116. The central pipe portion extends upward from a top surface 132 of the concave flange. The concave flange 130 includes a curved bottom surface 133 which engages the flesh of the patient. As seen here, the bottom surface is curved around one axis, and can correspond to a portion of a cylindrical wall, or can be described as having a barrel-vault shape.

Next, continuing with FIG. 12, the cylindrical handle 112 includes a top circular plane surface 154 and a handle sidewall 158. The perimeter 156 of the top plane surface 154 is chamfered. The handle sidewall 158 defines an upper end 150 and a lower end 152 of the handle. As seen here, the handle sidewall 158 surrounds the central pipe portion 116, or put another way the handle sidewall has a larger diameter than the central pipe portion. The handle sidewall 158 surrounds a cavity wall 162 that defines an internal cavity 160 of the cylindrical handle 112. The cavity wall extends from the upper end to the lower end of the handle, and is shorter than the length of the handle sidewall.

The cylindrical handle 112 includes ergonomic features which increase the overall user-friendliness of the injector 100. For example, the handle sidewall 158 can be sized to receive the fingers of a user's hand when the hand is placed generally on the upper end 150 of the cylindrical handle 112, as seen in FIG. 2. The cylindrical handle 112 also has a top circular plane surface 154 which will be oriented substantially parallel to the palm of a user's hand, and can be easily pressed. The chamfered perimeter 156 provides a smooth transition area from the top circular plane to the handle sidewall 158. These features of the cylindrical handle 112 provide a softer form language, like a button, which allows for a pressing motion.

Continuing with FIG. 12, the syringe assembly 114 is disposed within the internal cavity 160 of the cylindrical handle 112 and within the inner sidewall 124 of the body shield member 110. Specifically, an upper end 186 of the syringe assembly 114 is disposed within the internal cavity 160 and a lower end 188 is disposed within the inner sidewall of the central pipe portion 116.

The high-force compression spring 218 engages the top surface 154 at the upper end 150 of the handle 112. Generally, the high-force compression spring 218 will also engage the push disc of a plunger assembly that also includes a plunger head. Here, the push disc 192 is provided by the syringe slide 210, which engages the high-force compression spring 218. The plunger 190 is formed from a stem 198 and a head 196 at the bottom end of the stem. The plunger 190 is connected to the syringe slide 210 via screw 194. The plunger head 196 is located within the syringe barrel 212. The syringe barrel is hollow and has a volume for containing the fluid/pharmaceutical to be expelled by the injector. In particular embodiments, the volume of the barrel is about 0.3 cubic centimeters (cc).

The low-force compression spring 224 is located within the inner sidewall 124 of the body shield member and on a top surface 132 of the concave flange. The low-force compression spring 224 also acts on the syringe barrel 212 to ensure the needle is withdrawn back into the injector.

Needle 138 is located on the lower end of the syringe barrel 212, and exits through the orifice 142 through which fluid can exit the syringe barrel 212. The length and diameter of the needle can be of any desired size. The needle 138 is fitted or fixably attached to the syringe barrel 212 to form a leak-free connection. In particular embodiments, the needle is a 30 gauge needle.

The cavity wall 162 may include a slot 174 for holding a catch member 164. This function will be explained further herein.

FIG. 13 is an exterior side view of the injector in a fully depressed position. The handle 112 has been moved downwards towards the concave flange 130. The needle is visible, and extends out of the orifice for a length D. FIG. 14 is an identical exterior side view, but with line BB added (included because the needle is difficult to see).

FIG. 15 is a front cross-sectional view taken along line BB of FIG. 14. Initially, in comparing FIG. 12 to FIG. 15, it is noted that the internal components of the injector are not radially symmetrical, but rather there are different components aligned along the two perpendicular axes normal to the central axis 105. In FIG. 15, the bottom surface 133 of the concave flange is visible. Two bores 146 are also visible in the body shield member 110. The bores 146 are aligned with sockets 182 in the cylindrical handle 112. The bores 146 slidably receive fasteners 148, such as shoulder bolts, that engage the sockets 145 and prevent the body shield member 110, the cylindrical handle 112, and the syringe assembly 114 from separating under the spring loads exerted by low-force compression spring 224 and high-force compression spring 218.

As can also be seen in FIG. 15, the range of travel of the cylindrical handle 112 is limited by the engagement feature 134 of the central pipe portion 116 of the body shield member 110, which engages a mating feature 180 on the handle 112 to prevent the handle from being further depressed. The needle 138 contacts the stop wall 126 to stop its travel.

FIG. 16 provides further details on the plunger assembly. As previously noted, the high-force compression spring 218 will engage the push disc of a plunger assembly that also includes a plunger head. The plunger assembly can thus take several different forms. Here, the plunger assembly is formed from a syringe slide 210 and a plunger 190.

The syringe slide 210 includes a hollow central cylindrical protrusion 230 formed from a sidewall 234. A top wall 232 closes off the upper end of the hollow central cylindrical protrusion, and a threaded hole 238 is present in the top wall. The bottom 236 of the hollow central cylindrical protrusion is open. Located at the bottom edge of the hollow central cylindrical protrusion and surrounding the open bottom 236 is an annulet 240. The annulet 240 has a top surface 242 and a bottom surface 244. A second sidewall 246 extends upward from the outside diameter of the annulet 240 parallel to the protrusion sidewall 234, and concentrically surrounds the protrusion sidewall 234.

The plunger 190 is formed from a stem 198 and a head 196 at the bottom end of the stem. The stem 198 includes a threaded bore 248. The threaded bore 248 is arranged coaxially with the threaded hole 238 of the hollow central cylindrical protrusion 230, and the plunger 190 is connected to the syringe slide 210 via screw 194. The plunger 190 is thus disposed within the hollow central cylindrical protrusion 230.

The plunger head 196 is located within the syringe barrel 212. The syringe barrel is also located within the hollow central cylindrical protrusion 230, and engages the protrusion sidewall 234 via friction. This permits the syringe barrel and the syringe slide 210 to move relative to each other.

An optional retention disc 184 can be used to ensure that the syringe barrel does not slide out of contact with the syringe slide. The syringe barrel has a smaller diameter than the inside diameter of the annulet 240. The retention disc is in the shape of an annulus, and has a smaller inside diameter than the diameter of the syringe barrel. The retention disc can then be affixed to the bottom surface 244 of the annulet 240.

The high-force compression spring is advantageously arranged between the second sidewall 246 and the protrusion sidewall 234, simplifying manufacturing as well as increasing the stability of the high-force compression spring. The high-force compression spring 218 acts on the top surface 242 of the annulet 240, and the annulet thus acts as the push disc of this syringe assembly.

FIGS. 17-19 are front cross-sectional views illustrating the operation of the injector 100. FIG. 17 illustrates the start position, FIG. 18 illustrates the partially-depressed position, and FIG. 19 illustrates the fully-depressed position.

Starting at the start position depicted in FIG. 17, the user operates the injector 100 by placing the concave flange 130 at the desired injection site. The syringe assembly 114 is wholly contained within the body shield member 110 and the cylindrical handle 112. It is noted that the low-force compression spring 224 is at its greatest length. Also visible are the fasteners 148 within the bores 146.

Next, as illustrated in FIG. 18, the user presses the cylindrical handle 112 downwards to a partially depressed positon to start the injection process. The low-force compression spring 224 fully compresses, and the high-force compression spring 218 pushes the needle 138 through the needle sheath 140 and the orifice 142 and beyond the concave flange 130. The needle contacts the stop surface 136, which stops the needle from continuing to extend through the orifice. The distance the needle 138 can be exposed can thus be controlled. When used in conjunction with the concave flange 130, the needle cannot penetrate an infant's flesh too far so as to engage in the bone. The concave flange 130 stays in contact with the infant's limb because the force is applied by the user via the high and low-force compression springs 218, 224 to the body shield member, and thus reduces local compression of the flesh of the limb. In particular embodiments, the low-force compression spring 224 exerts approximately 50 grams of force, which is sufficient to penetrate the skin of a patient, such as an infant. At this point, the high-force compression spring 218 has compressed marginally, and not enough to begin expelling the fluid contained within syringe barrel 212. Also note that the fasteners 148 move through the bores 146 as the handle 112 is depressed.

Next, as illustrated in FIG. 19, the user continues to press the cylindrical handle 112 to a fully-depressed position. When the needle 138 contacts the stop surface 136, this causes the syringe barrel 212 to also be stopped vertically, so the barrel can no longer descend. However, the handle and the high-force compression spring 218 are still causing the syringe slide 210 to continue descending. The high-force compression spring 224 compresses until the mating feature 180 of the cylindrical handle 112 engages with the engagement feature 134 of the body shield member 110. In particular embodiments, the force required for the high-force compression spring 224 to completely compress is approximately 150 grams.

As a result, the plunger head 196 pushes through the syringe barrel to dispense the contents of the syringe barrel 212 through the needle 138. The high-force compression spring 224 acts on the push disc 192, which is joined to the plunger head 196. The plunger head 196 sealingly engages and slides within the syringe barrel 212 to express the drug.

The distance the plunger 190 and plunger head 196 travel in the syringe barrel 212 is a few millimeters because the expected amount of drug to be dispensed is very low (for example, 0.3 cc for proper dosing for infants). It can take approximately 2-3 seconds to express 0.3 cc of drug through the needle 138 and to the patient. In use, the user or care giver is instructed to count for 5 seconds before they remove the injector device from the infant's limb. Again, note that the fasteners 148 continue to move through the bores 146. At the end of the stroke when the contents of the syringe barrel are completely dispensed, the device subsequently returns to the start position to retract the needle into the orifice, lock the handle into the start position, and shield the user from the needle to minimize exposure.

Figure 24:
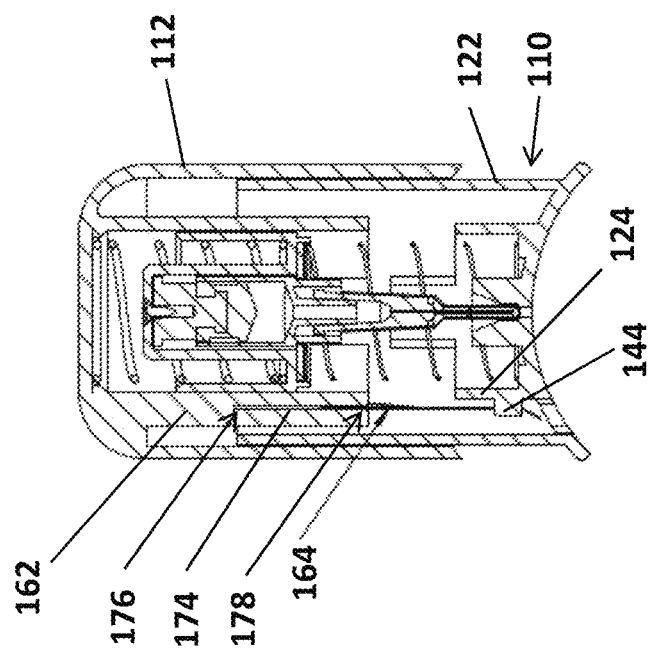
FIG. 24 is a side-cross sectional view taken along the line EE of FIG. 23, showing the catch member engaged to lock the injector in its start position.
Figure 23:
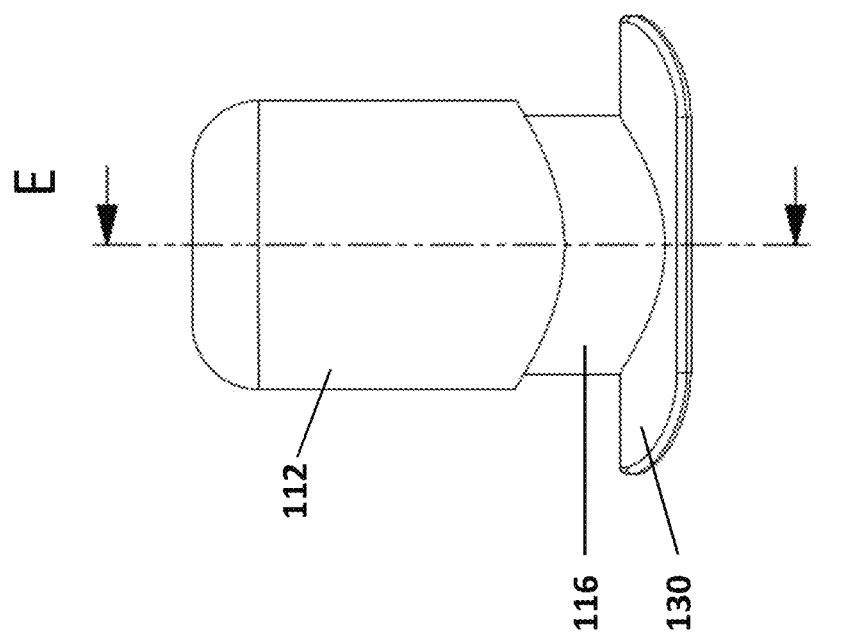
FIG. 23 is a front exterior view showing the first exemplary embodiment of an injection device of the present disclosure after returning to the start position from the fully-depressed position of FIG. 20.

FIGS. 20-24 illustrate the operation of the catch member 164 in keeping the injector from being reused. FIG. 20 is an exterior front view of the injector in a fully depressed position. The handle 112 has been moved downwards towards the concave flange 130, and the central pipe portion 116 is barely visible. FIG. 21 is a side cross-sectional view taken along line DD of FIG. 20. FIG. 22 is a view of the catch member 164 itself. FIG. 23 is an exterior front view of the injector after returning from the fully depressed position to the start position. The central pipe portion 116 is now much more visible. FIG. 24 is a side cross-sectional view taken along line EE of FIG. 23.

Referring initially to FIG. 21, the body shield member 110 and the cylindrical handle 112 are visible. The outer sidewall 122 and the inner sidewall 124 of the body shield member are also shown. A boss 144 extends from the outer surface of the inner sidewall 124, near the bottom end of the body shield member. The cavity wall 162 of the cylindrical handle 112 includes a slot 174 in which the upper end of the catch member 164 is stowed. The slot itself includes an upper end 176 and a lower end 178.

FIG. 22 shows the catch member 164 itself. The catch member includes a generally flat portion, with an angular bend at the lower end 168. Located at the upper end 166 of the catch member 164 is a spring tab or bent arm 170, extending upward and away from the flat portion. A hole 172 is located at the lower end 168 of the catch member 164.

Now referring back to FIG. 21, the catch member 164 is stowed in the slot 174. The bent arm 170 engages the slot 174, holding the catch member 164 in place by friction. The lower end of the catch member remains exposed. As illustrated here, in the fully-depressed position, the hole 172 of the catch member 164 engages the boss 144.

Referring now to FIG. 24, as the cylindrical handle 112 moves back to the start position, this engagement between the hole 172 and the boss 144 pulls the catch member 164 downwards out of the slot 174. The bent arm 170 expands outward toward the central axis of the body shield member 110 when freed from the slot 174. The bent arm 170 creates a mechanical interference against the bottom of the cavity wall 162 to prevent the cylindrical handle 112 from being pressed down again, thereby eliminating the risk of exposing a used needle. It is noted that the portion of the upper end of the catch member above the bent arm 170 remains within the slot, to maintain the strength of the mechanical interference.

Figure 27:
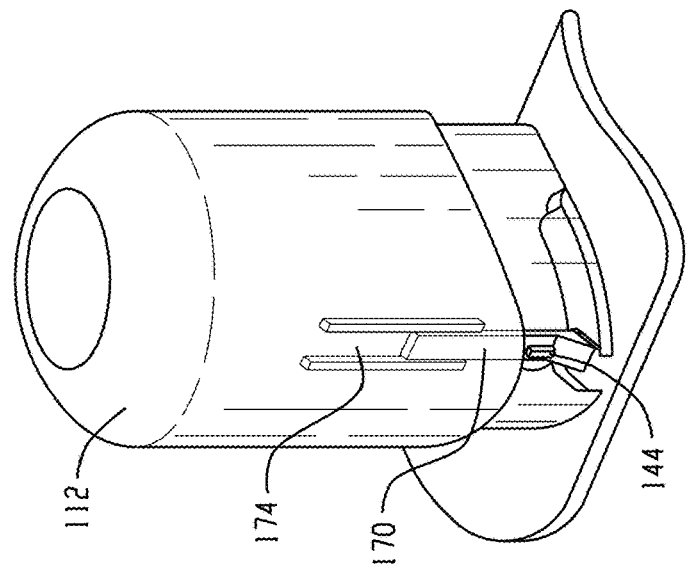
FIG. 27 is a perspective view showing the catch member in the start position after returning from the fully-depressed position.
Figure 26:
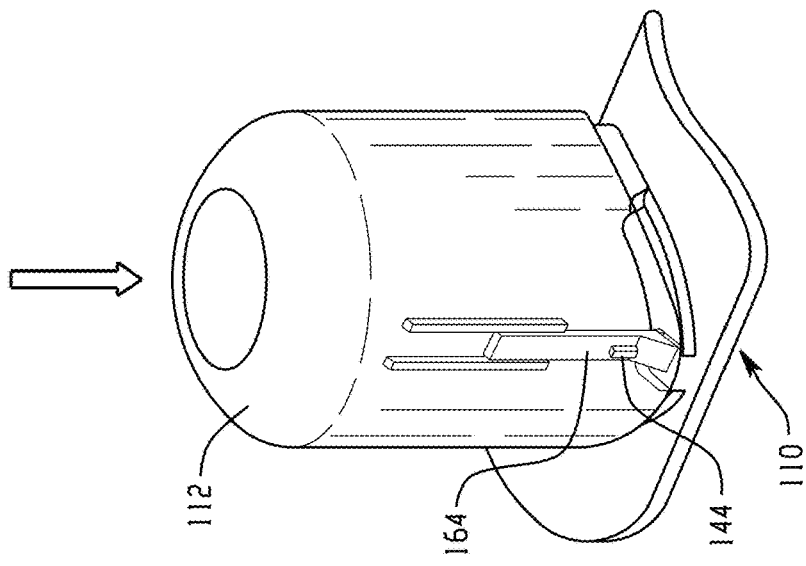
FIG. 26 is a perspective view showing the catch member in the fully-depressed position.
Figure 25:
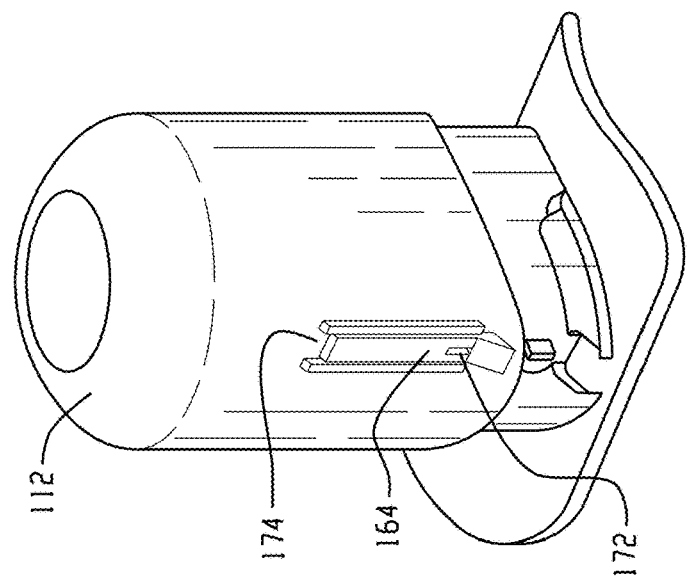
FIG. 25 is a perspective view showing the catch member in the start position.

FIGS. 25-27 show an alternative view in the process of locking the cylindrical handle 112 in the start position with the catch member 164. In FIG. 25, the injector is in its start position and the catch member 164 is shown in its held position within the slot 174 of the cylindrical handle 112. The hole 172 of the catch member is not within the slot, and is exposed. In FIG. 26, when the handle 112 is fully depressed, the hole of the catch member 164 engages the boss 144 of the body shield member 110. In FIG. 27, this engagement pulls the catch member out of the slot 174 as the injector returns to its start position from its fully deployed position. The bent arm 170 can then engage the cavity wall to prevent the handle from being depressed again.

Figure 28:
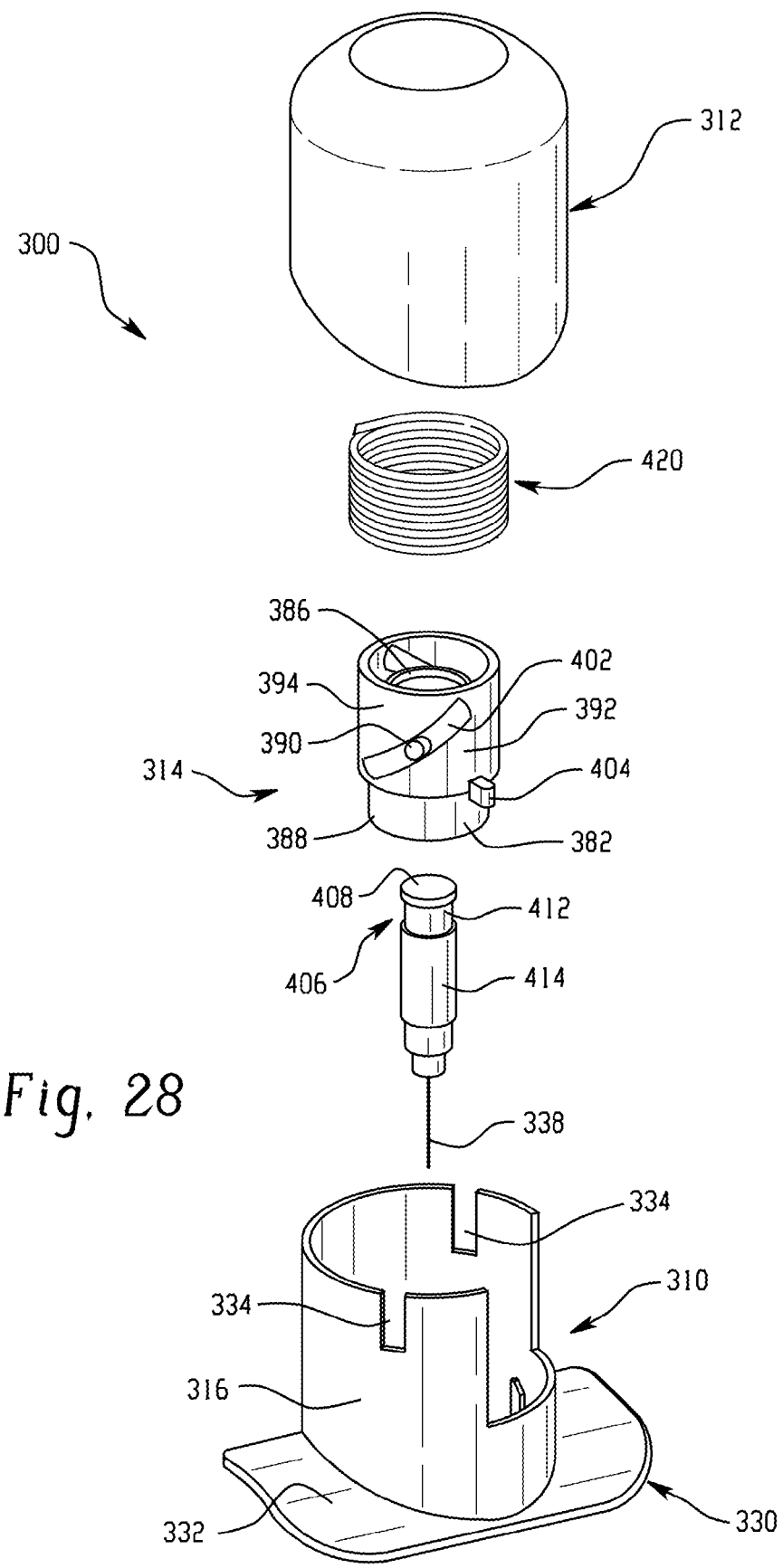
FIG. 28 is an exploded perspective view showing the components of a second exemplary embodiment of an injection device of the present disclosure.
Figure 29:
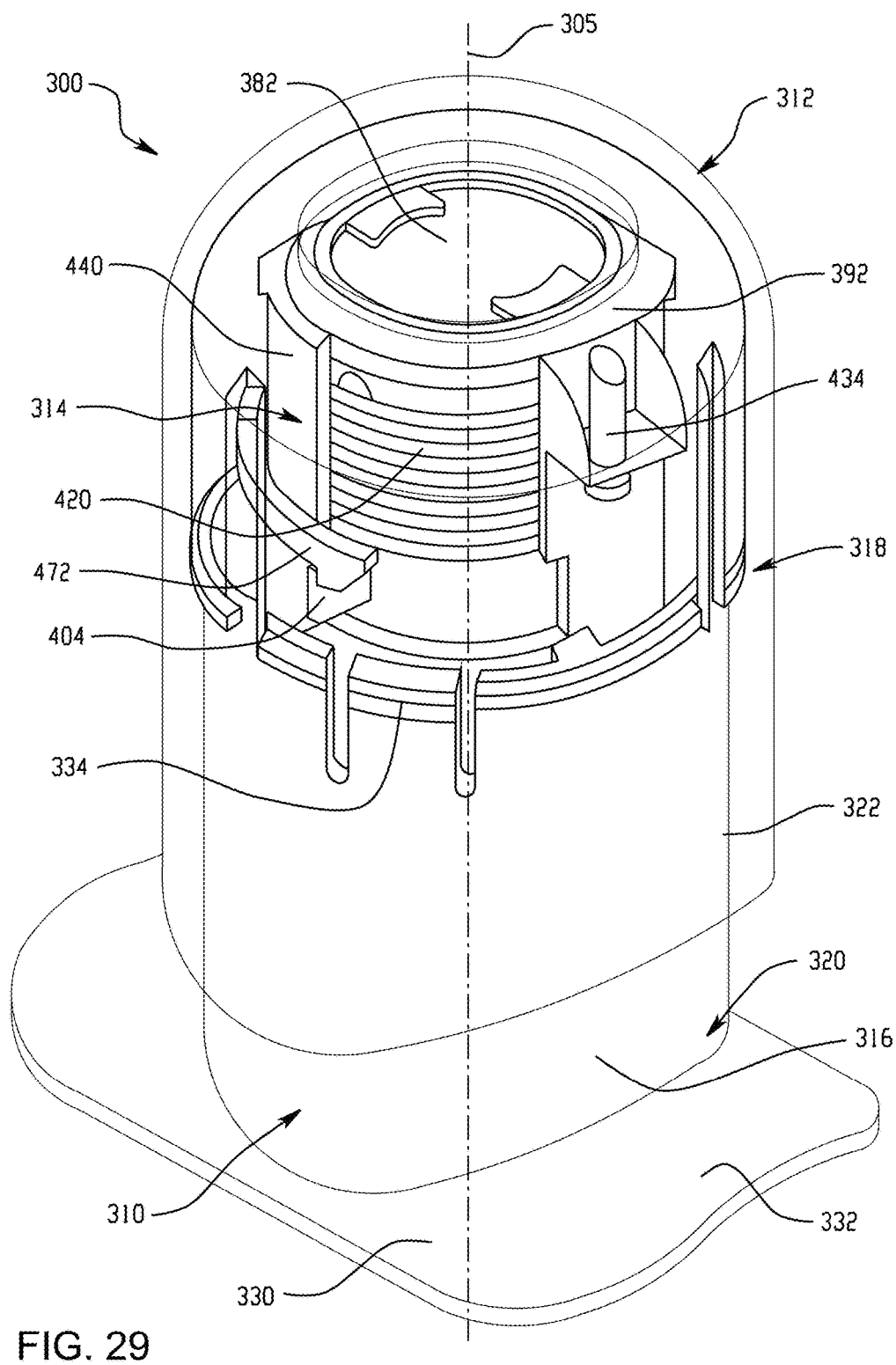
FIG. 29 is a perspective view showing additional components of the injection device of FIG. 28.

FIG. 28 is an exploded assembly drawing showing the various components of a second exemplary embodiment of an injection device 300 of the present disclosure. As illustrated, the injector 300 contains the three same main components: a body shield member 310, a cylindrical handle 312, and a syringe assembly 314 which are arranged vertically along a common central axis.

The cylindrical handle 312 and the body shield member 310 form the exterior components of the injector as shown. The syringe assembly 314 is disposed between the cylindrical handle 312 and the body shield member 310. Here, the syringe assembly is formed from a torsion spring 420, an inner barrel 382, a cylindrical outer sleeve 392 surrounding the inner barrel, a plunger 406, a syringe barrel 414, and a needle 338.

The body shield member 310 includes a concave flange 330 with a top surface 332. Extending upward from the concave flange is central pipe portion 316, which includes engagement features 334 for engaging the cylindrical handle 312.

The inner barrel 382 includes a sidewall 388 and a push wall 386. The push wall 386 engages the plunger 406. The sidewall 388 includes at least one pin 390 extending outwards therefrom. The pin engages a helical curved slot 402 in a sidewall 394 of the outer sleeve 392. A flange 404 extends outward from a lower end of the outer sleeve 392.

The plunger 406 includes a push disc 408 and a stem 412. The lower end of the stem includes the plunger head (not visible), which engages and travels through the syringe barrel 414. Although not seen here, the inner barrel 382 is hollow, and the plunger 406 and syringe barrel 414 are located within the inner barrel, similar to the structure described in FIG. 16.

In use, the upper end of the torsion spring 420 engages a boss in the handle 312. The lower end of the torsion spring 420 engages the flange 404 of the outer sleeve 392. The outer sleeve 392 maintains a minimum distance from the concave flange 330. The outer sleeve is also fixed in place, such that it cannot rotate completely, although it can still move up/down relative to the body shield member 110.

The handle 312 includes a pusher surface (not visible) that engages the push wall 386 of the inner barrel. As the handle 312 descends, the pusher surface pushes the inner barrel down. The torsion spring exerts a rotational force against the flange 404, causing the outer sleeve to rotate for a fixed distance. During this fixed distance, the pin 390 remains at the top of the helical curved slot 402. Both the inner barrel 382 and the outer sleeve 392 travel downwards, and this corresponds to the partially-depressed position, where the needle is pushed into the patient until hitting a stop surface.

Next, after the outer sleeve 392 is rotated for the fixed distance, it can no longer rotate. However, the pusher surface is still pushing the inner barrel 382 downward. This causes the pin 390 to begin traveling down the helical curved slot 402, and the plunger 406 passes through the syringe barrel 414 to expel the contents thereof.

Because the outer sleeve has been prevented from rotating, energy has been built up in the torsion spring. As the user releases pressure on the handle 312, this energy pushes the handle back upwards. This causes the outer sleeve 392, the inner barrel 382, the syringe barrel 414, and the needle 338 to all travel upwards as well, retracting the needle into the injector 300. As a result, no low-force compression spring is needed to cause retraction.

FIGS. 29-46 provide more detail on the second embodiment of the injection device 300. The injector 300 otherwise contains the three same main components as the previously described injection devices: a body shield member 310, a cylindrical handle 312, and a syringe assembly 314 which are arranged vertically along a common central axis 305. The body shield member 310 includes a concave flange 330 with a top surface 332. The body shield member 310 also includes a central pipe portion 316 extending upward from the concave flange 330.

Figure 30:
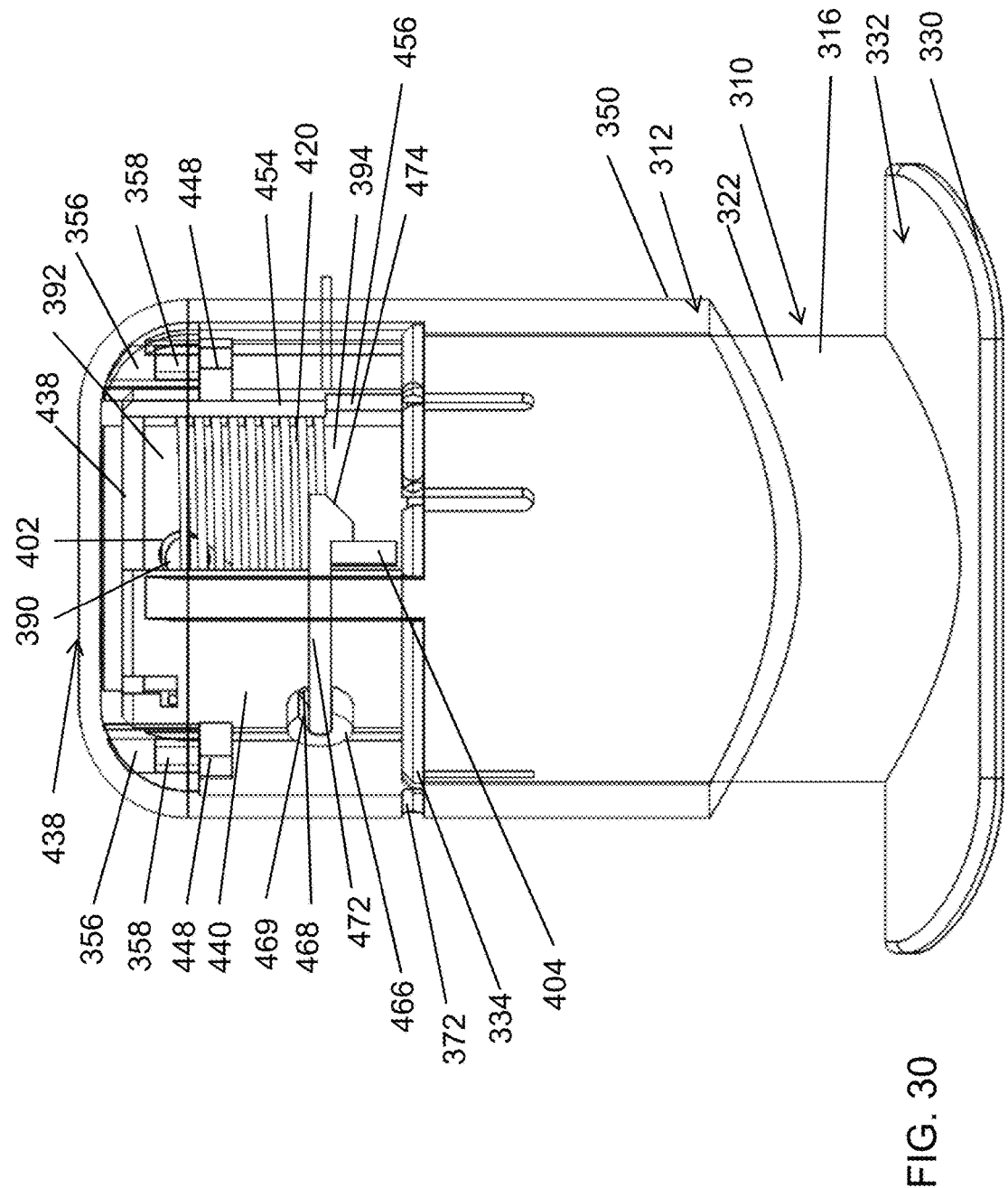
FIG. 30 is a front view of the second exemplary embodiment of an injection device of the present disclosure with the handle being transparent.

Continuing with FIG. 30, the injection device 300 is shown in an alternate front view with the cylindrical handle 312 being semi-transparent, allowing for a more clear view of the assembled injection device. One or more attachment flanges 356 located on the cylindrical handle 312 receive corresponding attachment flanges 448 on retainer 440. The handle attachment flanges 356 have a threaded bore 358 for receiving fasteners 434. The fasteners 434 extend through the threaded holes 450 of the retainer 440 to attach the retainer to the cylindrical handle 312. The fasteners 434 prevent these two main body parts from separating under the spring loads exerted by the low-force compression spring (not shown) and the torsion spring 420. The retainer 440 is cylindrical in shape and concentrically surrounds the outer cylindrical sleeve 392 and torsion spring 420. The retainer 440 also includes a catch arm 472 to prevent the outer sleeve 392 from rotating.

Catch arm 472 is rotably mounted to a rounded boss 466. The rounded boss 466 extends outwardly from a sidewall 446 of the retainer 440 and includes a cut-out portion 468. The cut-out portion 468 allows the catch arm 472 to rotate upward a distance which is limited by an angled top portion 469 of the cut-out. A hole (not shown) extends through the retainer sidewall 446 and is located in the center of the rounded boss 466. A pin (not shown) on the catch arm 472 fits into the hole of the rounded boss 466 so that the catch arm may rotate. Also seen in FIG. 30 is the flange 404, which extends outward from a lower end of the outer sleeve 392. The catch arm 472 has a tooth 474 for engaging the flange 404 of the outer sleeve 392. The pin 390 of the inner barrel (not shown) can also be seen as engaged with the helical curved slot 402 in a sidewall 394 of the outer sleeve 392.

Figure 31:
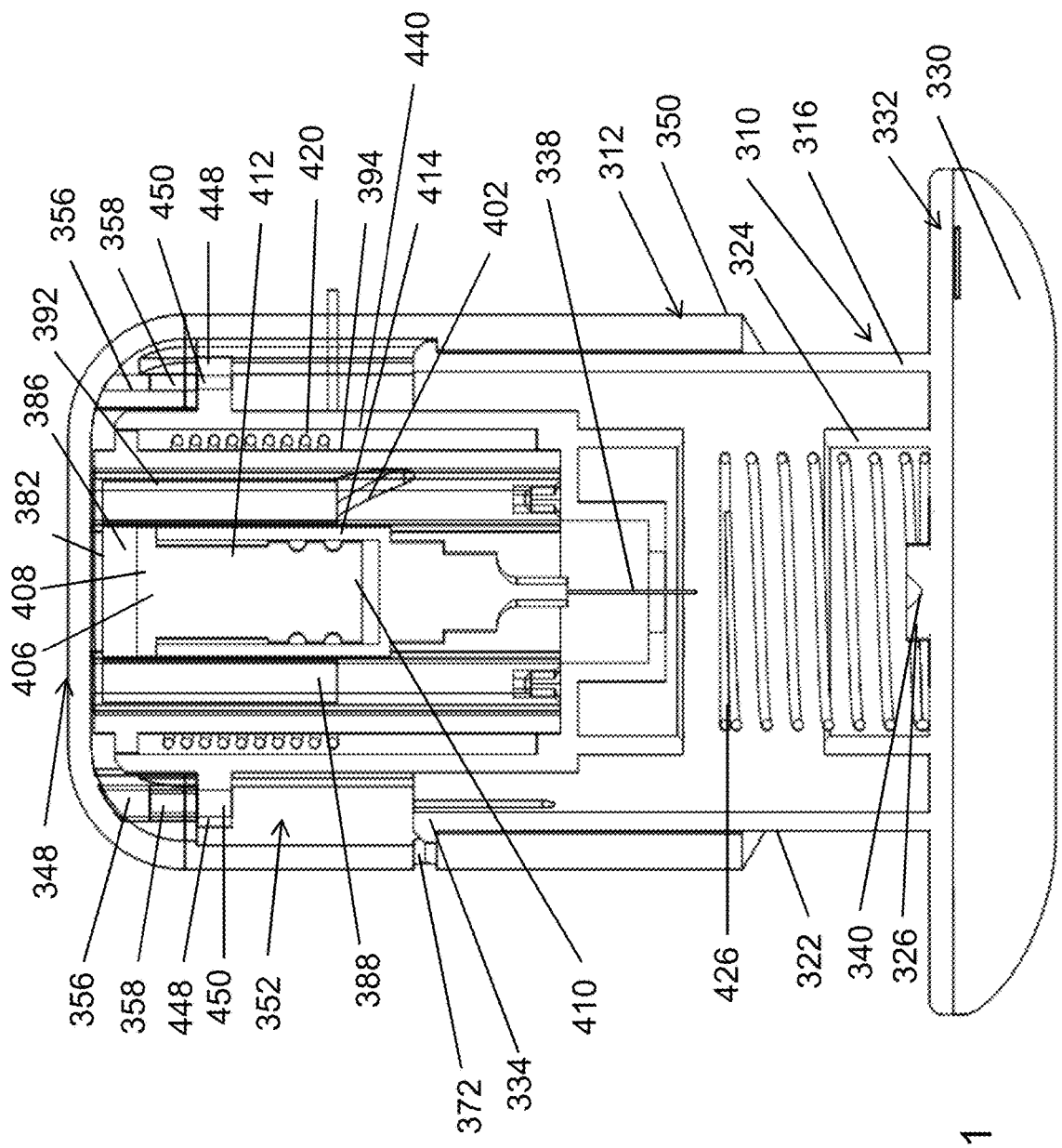
FIG. 31 is a front cross-sectional view of the second exemplary embodiment of an injection device of the present disclosure showing the syringe assembly and the low-force compression spring.

In FIG. 31, the injection device 300 is shown in an alternative cross-sectional front view whereby the syringe assembly 314 and low-force compression spring 426 can be seen. The syringe assembly 314 has three main components, including an inner barrel 382, an outer cylindrical sleeve 392 and a plunger assembly 406. The syringe assembly 314 is disposed within the internal cavity 352 of the cylindrical handle 312 and within the outer sidewall 322 of the body shield member 310. Specifically, an upper end 378 (FIG. 38) of the syringe assembly 114 is disposed within the internal cavity 352 and a lower end 380 (FIG. 38) is disposed within the outer sidewall of the central pipe portion 316. Inner barrel 382 is shown as being hollow and includes a sidewall 388 and a push wall 386.

One side of the push wall 386 of the inner barrel engages a pusher surface (not visible) on the handle 312. The other side of the push wall 386 engages the plunger 406. The plunger 406 is formed from a stem 412 and a head 410 at the lower end of the stem. The plunger head 410 engages and travels through the syringe barrel 414. The plunger 406 and syringe barrel 414 are located within the hollow portion of the inner barrel 382. The syringe barrel is hollow and has a volume for containing the fluid/pharmaceutical to be expelled by the injector. In particular embodiments, the volume of the barrel is about 0.3 cubic centimeters (cc).

Needle 338 is located on the lower end of the syringe barrel 414, and exits through the orifice 340 through which fluid can exit the syringe barrel. The length and diameter of the needle can be of any desired size. The needle 338 is fitted or fixably attached to the syringe barrel 414 to form a leak-free connection. In particular embodiments, the needle is a 30 gauge needle.

The low-force compression spring 426 is located within the inner sidewall 324 of the body shield member and on a top surface 332 of the concave flange. The low-force compression spring 426 also acts on the retainer 440 to ensure the needle is withdrawn back into the injector.

Figure 32:
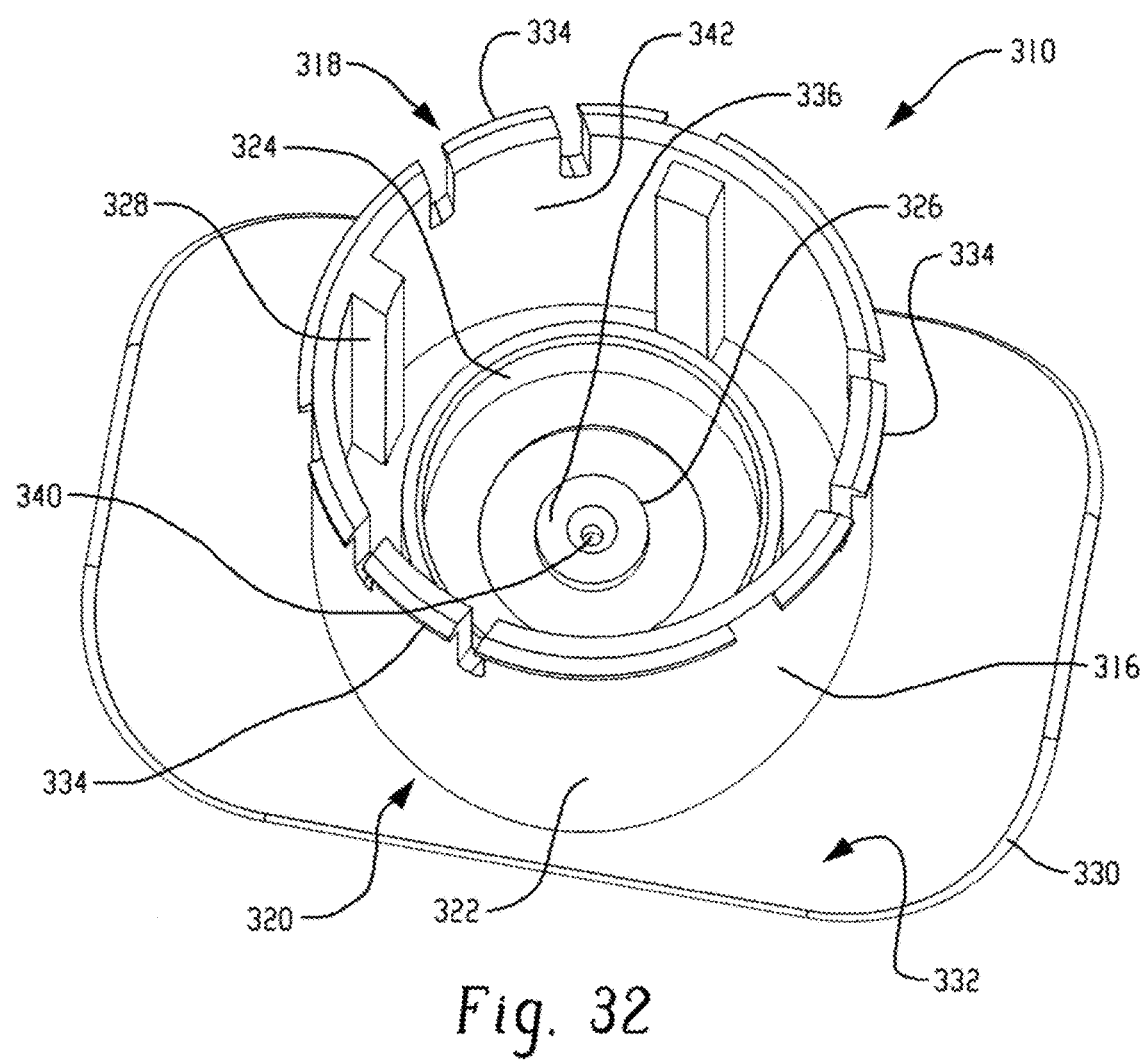
FIG. 32 is a top perspective view of the body shield member according to the second exemplary embodiment of an injection device of the present disclosure.
Figure 33:
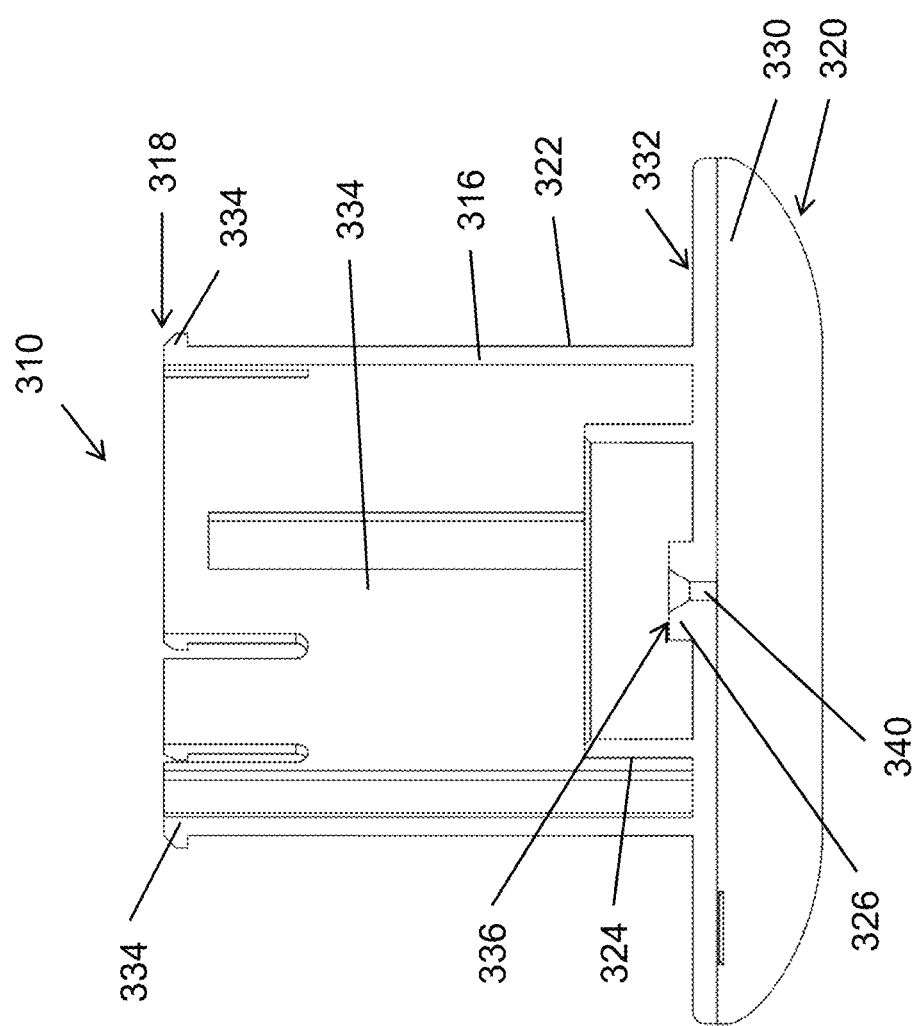
FIG. 33 is a cross-sectional front view of the body shield member of FIG. 32.
Figure 34:
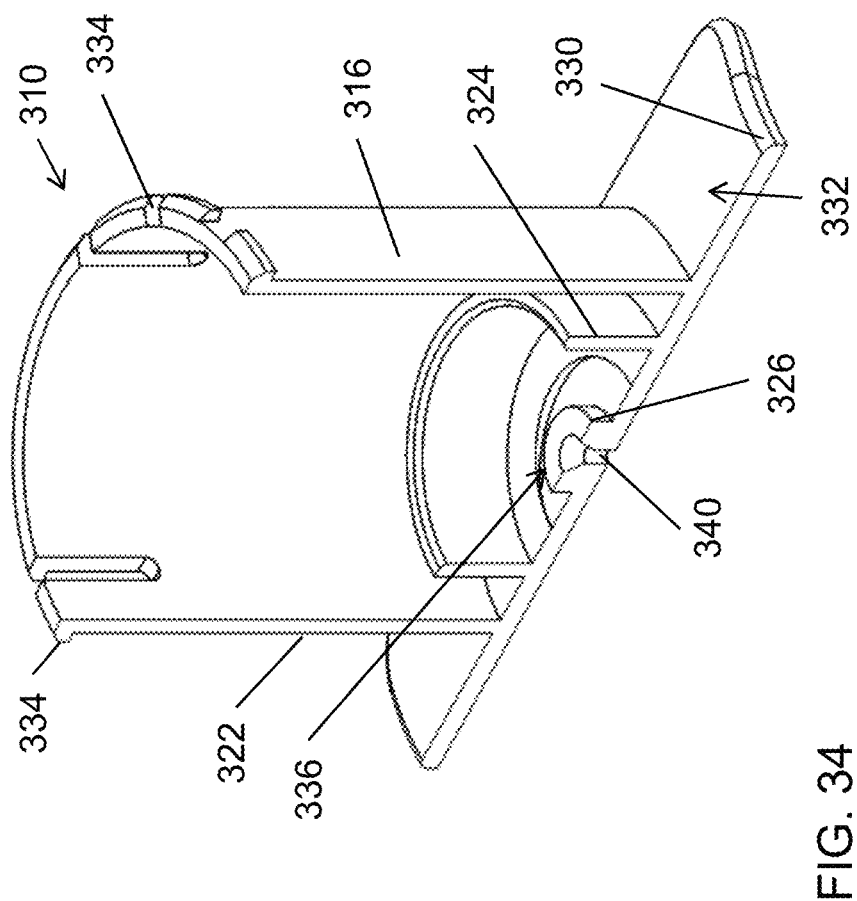
FIG. 34 is a cross-sectional side view of the body shield member of FIG. 32.

The body shield member 310 is more clearly shown in FIGS. 32-34. The central pipe portion 316 is formed from an outer side wall 322. Central pipe portion 316 includes engagement features 334 for snap fitting into a slot or mating feature 372 in the cylindrical handle 312. The outer sidewall 322 defines an upper end 318 and a lower end 320 of the central pipe portion 316 and body shield member. The outer sidewall 322 has an interior surface 342, on which a pusher column 328 is located. The pusher column 328 extends along the length of the sidewall 322 and acts to push the catch arm 472 upward upon depression of the injection device.

Disposed within the outer sidewall 322 of the central pipe portion 316 is a concentric inner sidewall 324. The inner sidewall is relatively shorter in height compared to the outer sidewall 322. Disposed within the inner sidewall 324 is a stop wall 326. The stop wall 326 has a stop surface 336 and surrounds an orifice 340. The stop wall 326 will engage the needle (not shown) to control the length of the needle that is exposed beyond the orifice. The orifice 340 extends through the concave flange 330, permitting the needle to pass from one side to the other.

The concave flange 330 is located on the lower end 320 of the body shield member 310. The concave flange 330 extends outwardly from both sides of the central pipe portion 316. The concave flange 330 includes a top surface 332 and curved bottom surface (not shown) which engages the flesh of the patient. The curved bottom surface of the concave flange 330 acts to control local tissue depression.

Figure 35:
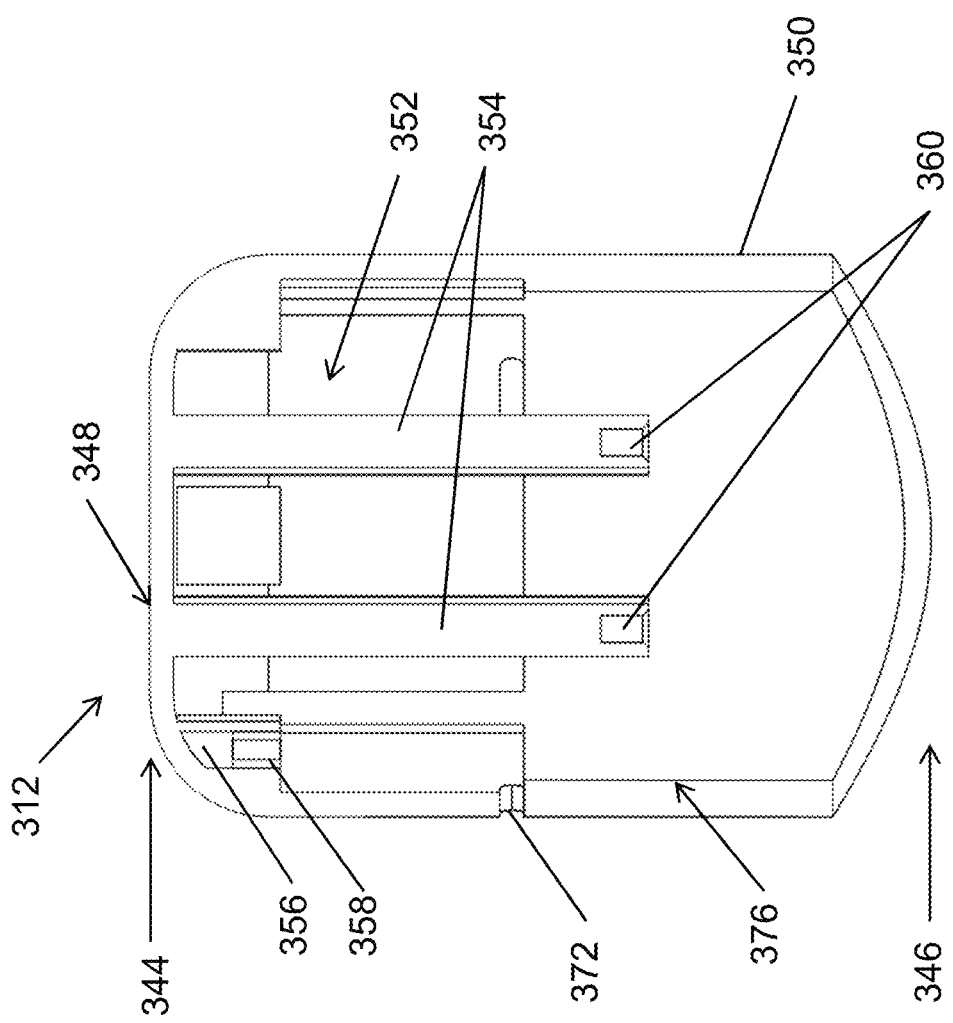
FIG. 35 is a cross-sectional front view of the cylindrical handle showing the internal features thereof according to the second exemplary embodiment of an injection device of the present disclosure.
Figure 36:
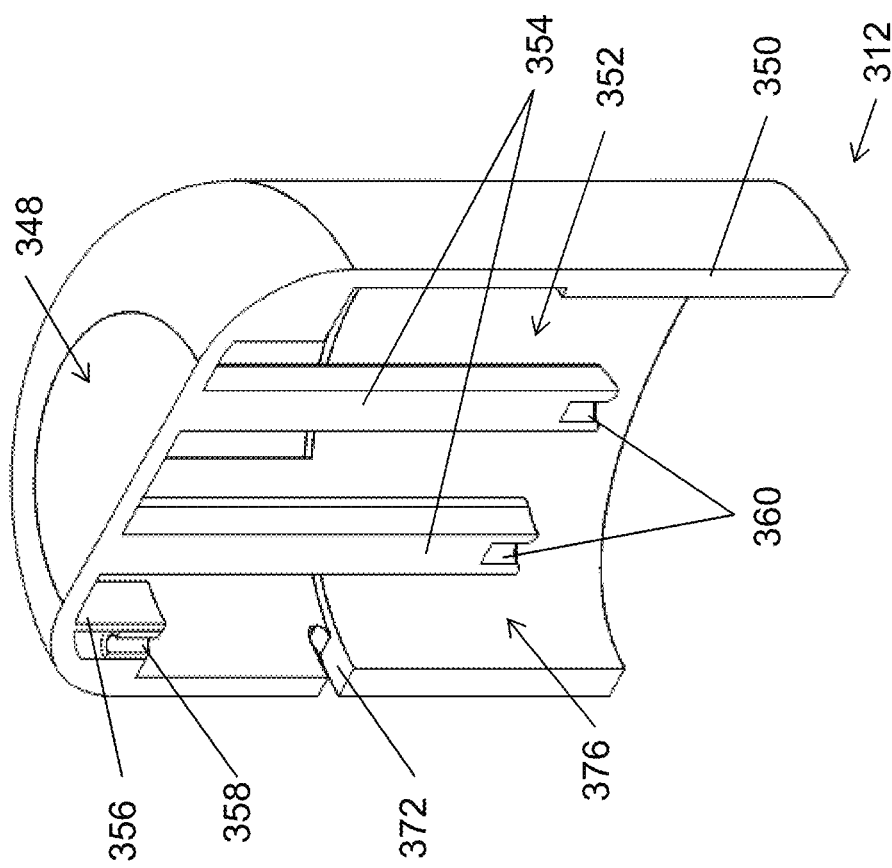
FIG. 36 is a cross-sectional perspective view of the cylindrical handle of FIG. 35.
Figure 37:
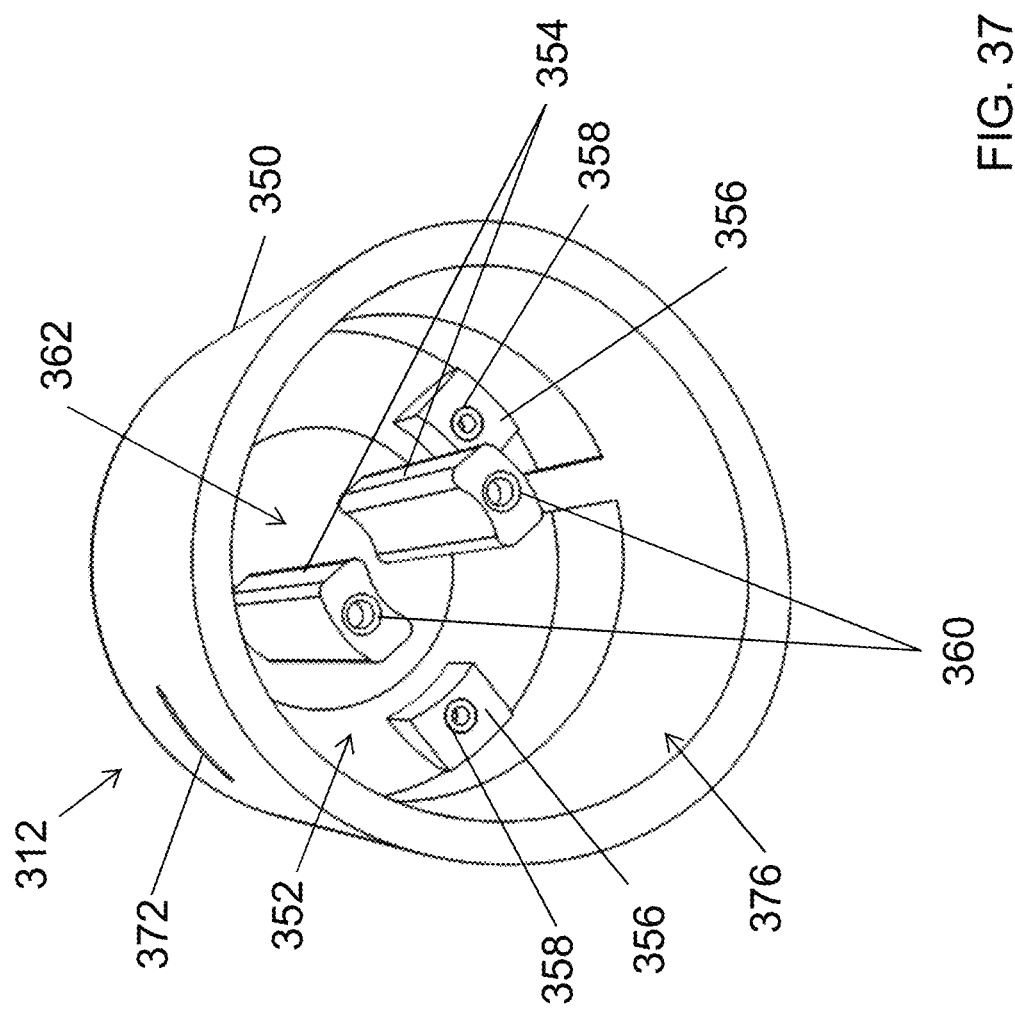
FIG. 37 is a bottom perspective view of the cylindrical handle of FIG. 35.

The cylindrical handle is more clearly shown in FIGS. 35-37. FIGS. 35 and 36 show a cross-sectional view front view and a cross sectional perspective view of the cylindrical handle 312. The cylindrical handle 312 includes a handle sidewall 350. The handle sidewall 350 surrounds an internal cavity 352, which acts to receive part of the spring assembly 314 when the injector is fully assembled. Extending through an interior surface 376 of the handle sidewall 350 is a mating feature 372, which can be in the form of hole or slit into which the engagement feature 334 of the central pipe portion 316 may snap into. The engagement of the engagement feature 334 with the mating feature 372 prevents the cylindrical handle 312 from depressing under minimal force and accidentally exposing the needle 338. Under the force applied when operating the injector, the engagement feature 334 slips out of the mating feature 372 so that the handle 312 may depress and activate the syringe assembly 314.

A top circular plane surface 348 is located on top of the cylindrical handle. Extending downward from the top circular plane surface 348 within the internal cavity 352 of the cylinder are one or more rails 354. A plunger pusher 382 of the syringe assembly 314 travels down rails 354 during operation of the injector. The rails 354 include attachment bores 360 for fixably attaching the cylindrical handle 312 to the retainer 440 at the lower end 346 of the handle. The rails 354 act to hold the syringe assembly 314 in place during operation of the injector.

FIG. 37 is a bottom perspective view of the cylindrical handle 312. The cylindrical handle includes a pusher surface 362, which is the bottom surface of the top circular plane surface (not shown). The pusher surface 362 engages the push wall of the inner barrel as the handle 312 descends, and pushes the syringe assembly 314 down.

Figure 38:
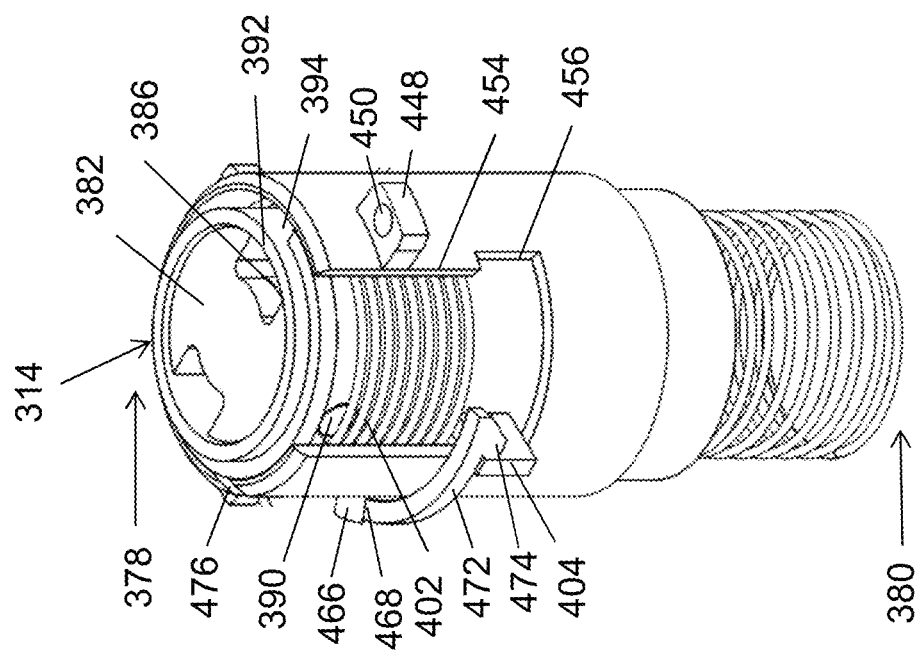
FIG. 38 is a perspective view of the syringe assembly showing the retainer surrounding the inner barrel, the outer cylindrical sleeve, and the plunger assembly according to the second exemplary embodiment of an injection device of the present disclosure.
Figure 39:
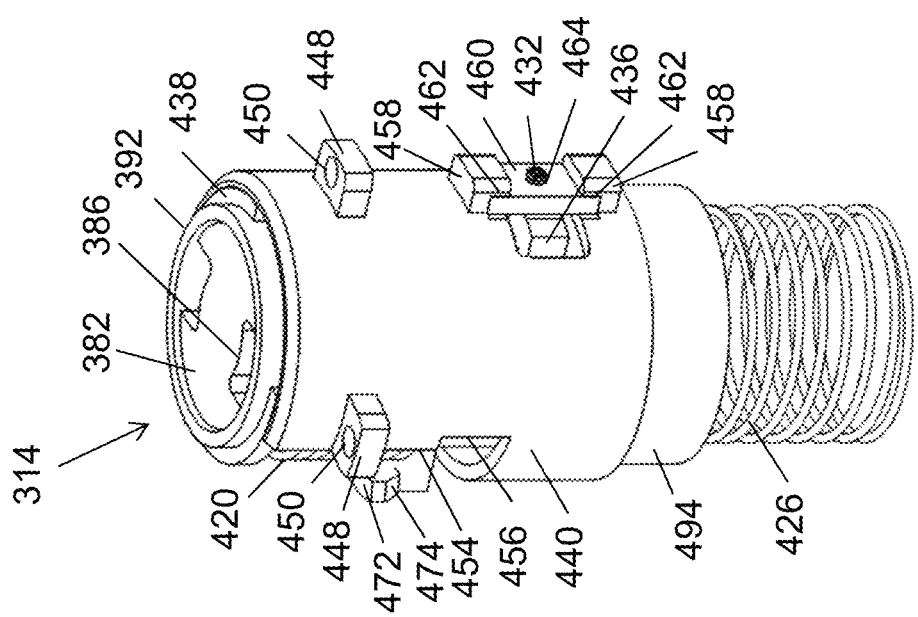
FIG. 39 is a perspective rear view of the syringe assembly of FIG. 38.
Figure 40:
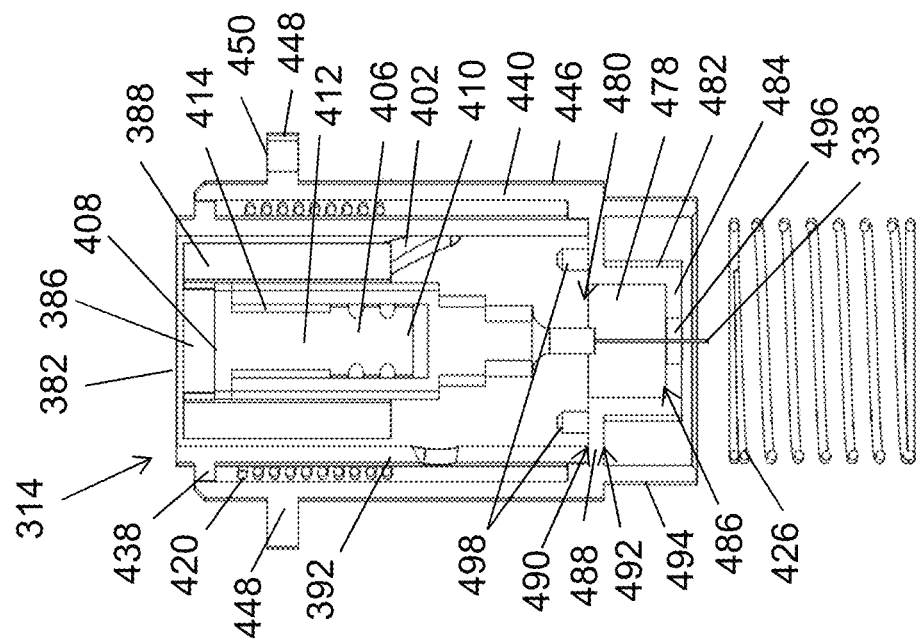
FIG. 40 is a cross-section front view of the syringe assembly of FIG. 38.

FIGS. 38-40 show the syringe assembly 314 with the retainer 440 concentrically surrounding the three main components, including the inner barrel 382, the outer cylindrical sleeve 392, and the plunger assembly (FIG. 40). The upper end 378 of the syringe assembly 314 is generally occupied by the retainer 440, inner barrel 382, cylindrical sleeve 392, and torsion spring 420. The lower end 380 of the syringe assembly 314 is generally occupied by the low-force compression spring 426.

The mating of the at least one curved slot 402 with the at least one pin 390, as shown in FIG. 38, allows the cylindrical sleeve 392 to rotate around the plunger pusher 382. A flange 404 extends outward from a lower end of the outer sleeve 392. The cylindrical sleeve 392 further includes a lip 438 located near the upper end 392 of the sleeve which substantially surrounds the perimeter of the sleeve. The lip 438 prevents the outer sleeve 392 from moving side to side against the retainer 440 during operation of the injection device.

The retainer 440 fixably attaches to the cylindrical handle 312 via the aforementioned retainer attachment flanges 448 and threaded bores 450. A sidewall 446 of the retainer 440 contains a relief notch 454 and flange notch 456. Relief notch 454 is optional and is provided mainly for ease of assembly of the injector device. The flange notch 456 receives the flange 404 of the outer cylindrical sleeve 392 during operation of the injection device.

As seen in FIG. 39, the retainer 440 includes plate flanges 458 which define a plate recess 462 for slidably receiving a plate 460. The plate 460 includes a threaded hole 464 for receiving a set screw 432. The set screw 432 engages with a tab feature 436 on the retainer 440. When the set screw 432 is screwed into the plate 460, it advances toward the tab feature 436 and pushes the tab inward toward the outer cylindrical sleeve 392. The tab 436 presses against the sidewall 394 of the outer sleeve 392, creating a friction force. The friction force acts to prevent unintended rotation of the outer cylindrical sleeve 392.

FIG. 40 is a front view cross section of the syringe assembly 314 surrounded by the retainer 440. Specifically, the plunger assembly 406 is located within the inner barrel 382, which is surrounded by the cylindrical sleeve 392, which is surrounded by the retainer 440.

Figure 41:
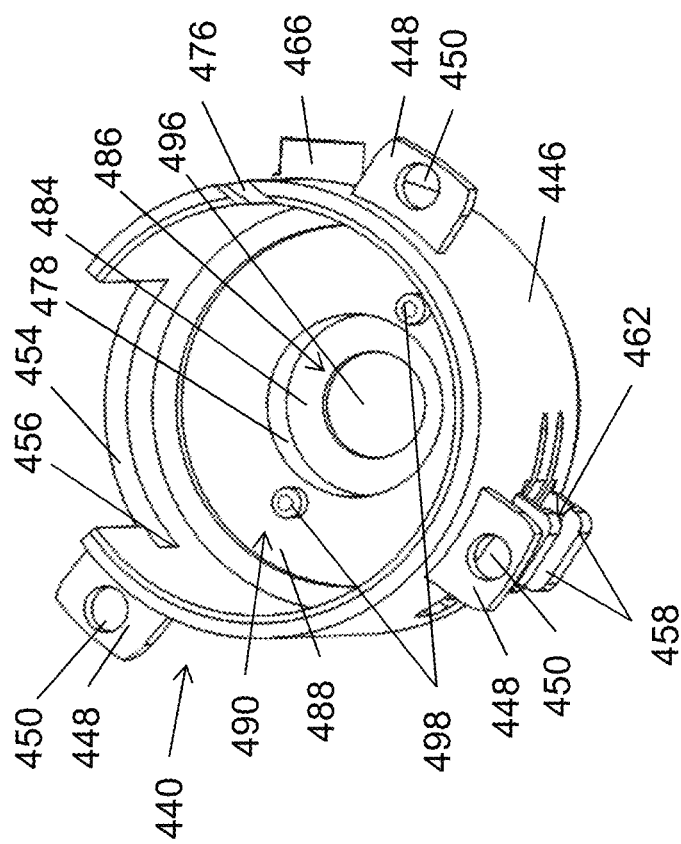
FIG. 41 is a top perspective view of the retainer showing the various engagement features thereof according to the second exemplary embodiment of an injection device of the present disclosure.
Figure 42:
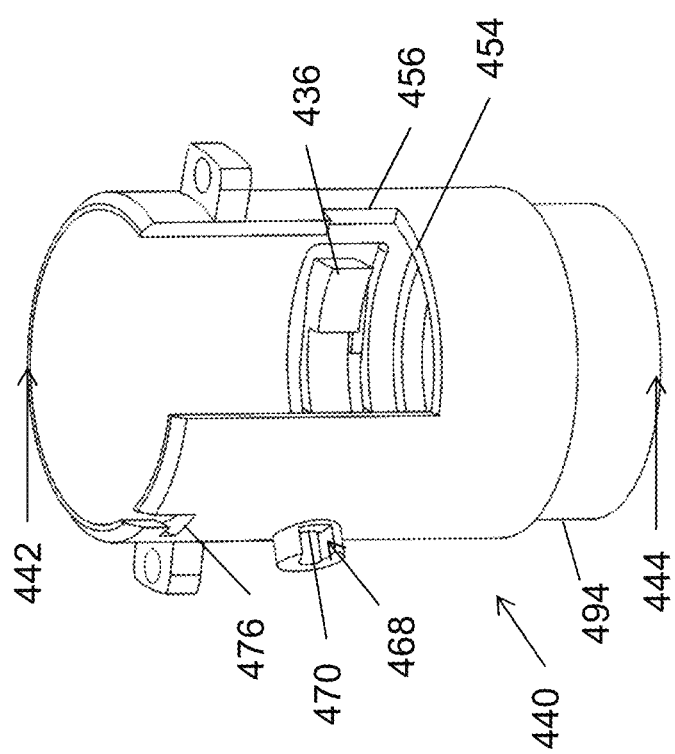
FIG. 42 is an additional perspective view of the retainer of FIG. 41.
Figure 43:
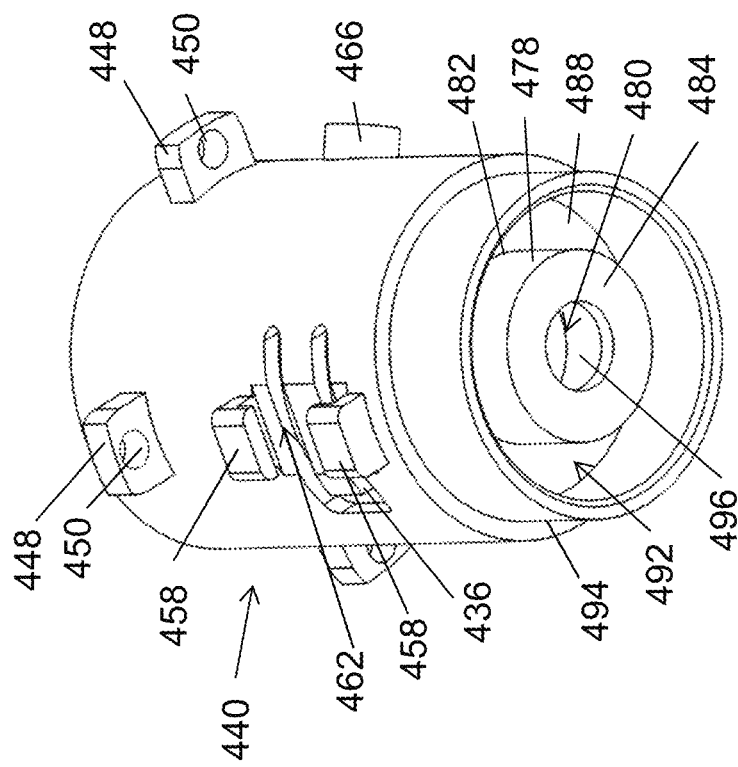
FIG. 43 is a bottom perspective view of the retainer of FIG. 41.

Additional features of the retainer 440 can be seen in FIGS. 41-43. The upper end 442 (FIG. 42) of the retainer 440 is shown having a torsion spring notch 476. The torsion spring notch 476 prevents an upper end (not shown) of the torsion spring (not shown) from moving. In FIGS. 40-43, the lower end 444 (FIG. 42) of the retainer 440 is shown with various engagement features. In particular, a hollow cylindrical protrusion 478 extends downward toward the low-force compression spring 426 as shown in FIG. 40. The hollow protrusion 478 has an open plane end 480 which receives a part of the plunger assembly 406, and partially closed plane end or bottom wall 484 which includes a needle hole 496 for exposing the needle 338. The bottom wall 484 has a stop surface 486 which engages with a portion of the syringe barrel 414 during operation of the injection device to prevent further downward travel. A sidewall 482 extending between the open plane end 480 and the bottom wall 484 defines the body of the hollow protrusion 478. An annulet 488 surrounds the open plane end 480 of the hollow cylindrical protrusion 478. A top surface 490 of the annulet 488 has one or more dowels 498 protruding upward from the top surface. The dowels 498 engage with the bores 360 of the rails 354 during operation of the injection device. A bottom surface 492 of the annulet engages with the low-force compression spring 426 during operation of the injector device. An annulet sidewall 494 extends downward from the outermost edge of the annulet 488. The annulet sidewall 494 generally extends a distance further than that of the sidewall 482 of the hollow cylindrical protrusion 478. The annulet sidewall 482 surrounds the low-force compression spring 426 when the injection device is depressed.

Figure 45:
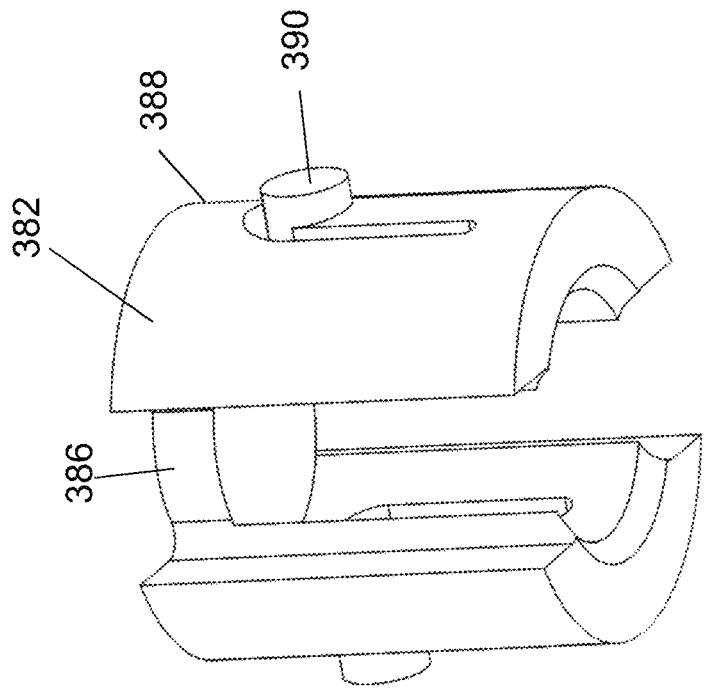
FIG. 45 is a bottom perspective view of the inner barrel of FIG. 44.
Figure 44:
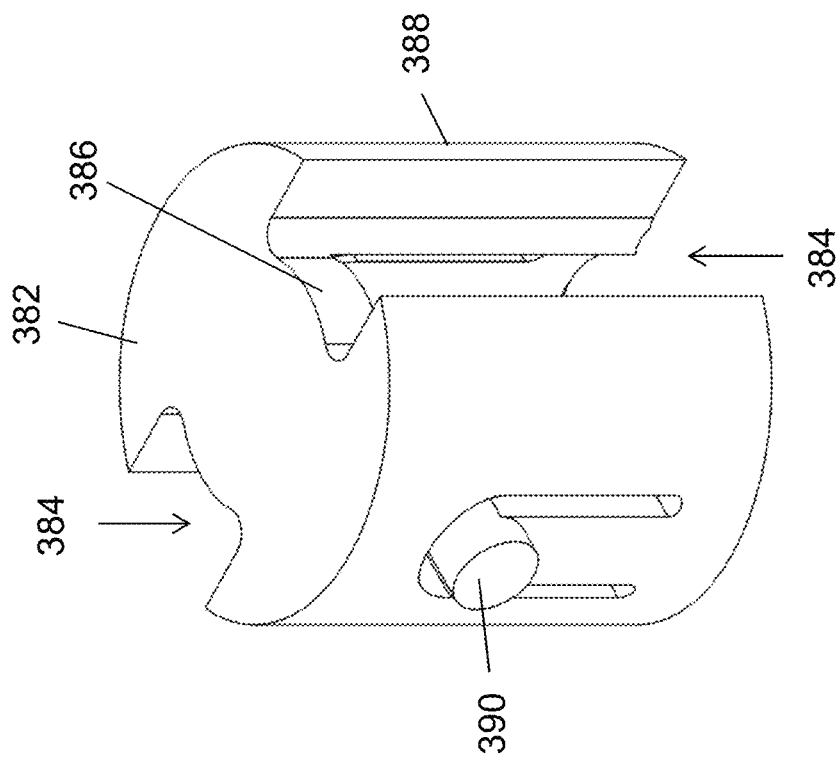
FIG. 44 is a perspective view of the inner barrel shown as being hollow and including a sidewall and push wall according to the second exemplary embodiment of an injection device of the present disclosure.

The specific features of the inner barrel 382 can be seen in FIGS. 44-45. Inner barrel 382 is shown as being hollow and includes a sidewall 388 and a push wall 386. The push wall 386 engages the plunger 406. The inner barrel 382 is in the shape of an I or barbell so that the inner barrel may travel down the one more rails 354 on the cylindrical handle 312. The pin 390 of the inner barrel 382 can also be seen.

Figure 46:
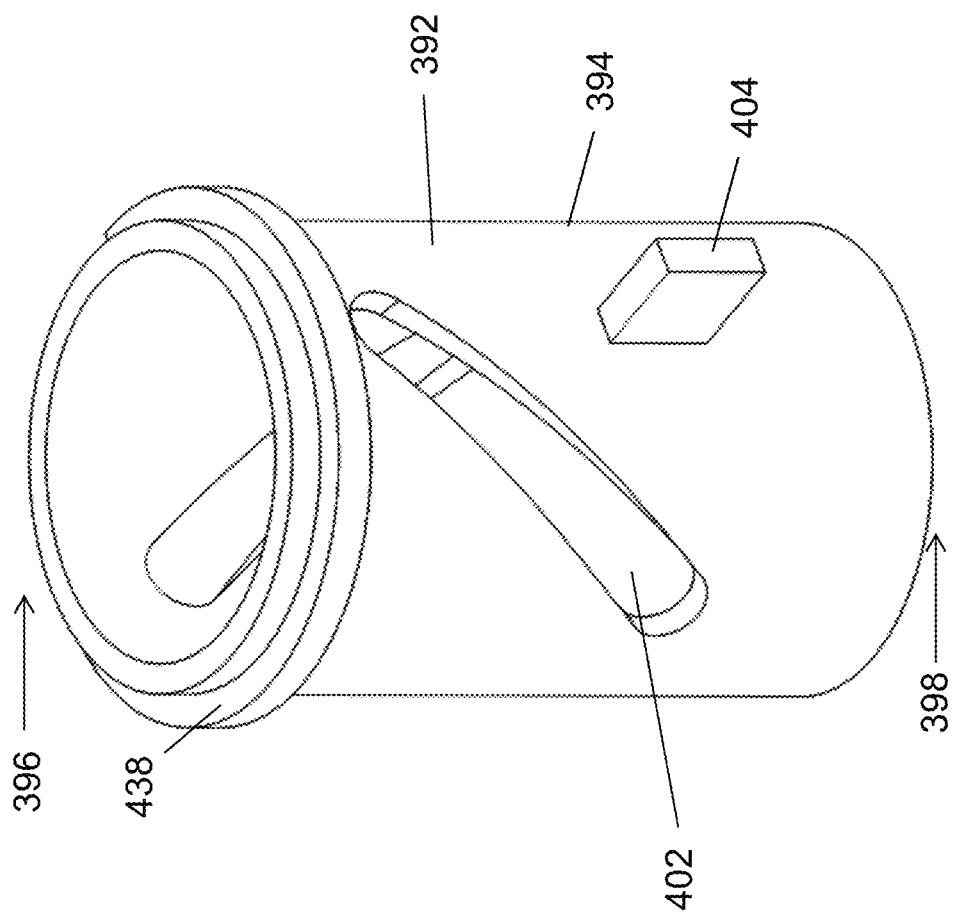
FIG. 46 is a perspective view of the cylindrical sleeve showing the at least one curved helical slot and sleeve sidewall according to the second exemplary embodiment of an injection device of the present disclosure.

Referring to FIG. 46, the cylindrical sleeve 392 has at least one curved helical slot 402 within a sleeve sidewall 394 that extends generally from an upper end 396 to a lower end 398 of the cylindrical sleeve. The cylindrical sleeve 392 further includes a lip 438 located near the upper end 392 of the sleeve which substantially surrounds the perimeter of the sleeve. Flange 404 can also be seen extending outward from the lower end 398 of the outer sleeve 392.

In use, referring back to FIGS. 29-31, when the handle 312 is in a start position, the low-force compression spring 426 biases the syringe assembly 314 apart from the body shield 310. The upper end of the torsion spring 420 engages the torsion spring notch 476 in the handle 312. The lower end of the torsion spring 420 engages the flange 404 of the outer sleeve 392. The torsion spring 420 is preloaded to exert a rotational force against the flange 404. However, the engagement of the tooth 474 of the catch arm 472 with the flange 404 initially prevents the outer sleeve 392 from rotating due to the force of the torsion spring 420. The outer sleeve 392 maintains a minimum distance from the concave flange 330. The outer sleeve 392 also maintains a distance from the retainer 440 due to the lip 438. The retainer tab 436 holds the outer sleeve 392 in place. The outer sleeve 392 being fixed in place, it cannot rotate completely, although it can still move up/down relative to the body shield member 310.

As the handle 312 descends into a partially depressed position, the lower end of the syringe assembly 380 engages the stop wall of the body shield member 310, and the needle 338 is exposed below the concave flange. More particularly, the pusher surface 362 of the handle 312 engages the push wall 386 of the inner barrel 382. The pusher surface 362 pushes the inner barrel 382 down along its rail slots 384 and the rails 354 of the cylindrical handle 312. The rails 354 also hold the inner barrel 382 in place and prevent it from rotating. The pin 390 remains at the top of the helical curved slot 402. The inner barrel 382, outer sleeve 392, torsion spring 420, and retainer 440 travel downwards with the handle 312 until the aforementioned engagement features on the lower end 444 of the retainer compress the low-force spring 426 and the stop surface 336 of the stop wall 326 engages the syringe barrel 414. This corresponds to the partially-depressed position, where length of the needle 338 that is exposed beyond the orifice 340 is controlled. The orifice 340 extends through the concave flange 330, permitting the needle 338 to pass from one side to the other, pushing into the patient.

Next, at the moment the stop surface 336 and syringe barrel 414 engage, the pusher column 328 has pushed the catch arm 472 upward so that the tooth 474 disengages from the flange 404 of the outer cylindrical sleeve 392. Once the tooth 474 disengages from the flange 404, the preloaded force of the torsion spring 420 can act on the flange 404. This force is greater than the frictional force acting on the sleeve 392 due to the tab 436 of the retainer 440 pressing against the sleeve, and causes the sleeve to rotate until the flange 404 engages the flange notch 456 of the retainer 440. As the sleeve 392 rotates, the curved helical slot 402 acts as a screw due to the engagement of the pin 390 of the inner barrel 283 with the slot. This causes the pin 390 to travel down the helical curved slot 402, and the plunger 406 passes through the syringe barrel 414 to expel the contents thereof. This corresponds to the handle 312 being a fully depressed position.

As the user releases pressure on the handle 312, the low-force compression spring pushes the handle back upwards toward the start position. This causes the retainer 440, the outer sleeve 392, the inner barrel 382, the syringe barrel 414, and the needle 338 to all travel upwards as well, retracting the needle into the orifice 340 of the injector 300.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. An injector for delivering a dose of a pharmaceutical, comprising:
   (a) a body shield member for engaging a limb, comprising:
      a concave flange on a lower end of the body shield member; and
      a stop wall surrounding a orifice and having a top surface which controls the exposure depth of a needle;
   (b) a cylindrical handle that travels along a central axis relative to the body shield member, comprising:
      a top circular plane surface on an upper end of the handle; and
      an internal cavity that extends between an upper end and a lower end of the handle;
   (c) a syringe assembly having an upper end and a lower end, the upper end being disposed within the internal cavity of the handle against the top circular plane surface, the lower end disposed within the body shield member, the syringe assembly comprising:
      a plunger assembly having a push disc and a head;
      a syringe barrel between the plunger assembly head and the needle;
      a high-force compression spring between the upper end of the handle and the push disc of the plunger assembly; and
      a low-force compression spring between the syringe barrel and a top surface of the concave flange, wherein the low-force compression spring biases the handle apart from the body shield member.

2. The injector of claim 1, wherein:
   (a) the body shield member further comprises a boss; and
   (b) the cylindrical handle further comprises:
      a catch member having a bent arm, and a hole for engaging the boss; and
      a slot for housing the catch member;
   wherein during use, the hole of the catch member engages the boss of the body shield member, the catch member is pulled out of the slot, and the bent arm engages a bottom surface of the cylindrical handle to prevent the handle from being depressed again.

3. The injector of claim 1, wherein the plunger assembly is formed from a syringe slide and a plunger stem;
   wherein the syringe slide comprises a hollow center body having a top wall and an open bottom, an annulet surrounding the open bottom that has a top surface and a bottom surface, and a sidewall extending upward from an outside diameter of the annulet;
   wherein an upper end of the plunger stem is fixed in place within the hollow center body of the syringe slide, and the plunger head is located at a lower end of the plunger stem; and
   wherein the lower end of the high-force compression spring engages the top surface of the annulet, which acts as the push disc of the plunger assembly.

4. The injector of claim 1, wherein the body shield member further comprises an engagement feature on an upper end of an outer sidewall, the cylindrical handle further comprises a mating feature, and the engagement feature engages the mating feature when the handle is in a fully depressed position.

5. The injector of claim 1, wherein an upper end of the low-force compression spring engages a lower end of the syringe barrel.

6. The injector of claim 5, wherein the upper end of the low-force compression spring contacts a retention disc that acts against the lower end of the syringe barrel.

7. The injector of claim 1, further comprising a safety pull which prevents the cylindrical handle from moving towards the concave flange of the body shield member when the safety pull engages the body shield member.

8. The injector claim 7, wherein the safety pull comprises a cover surface for covering the orifice of the body shield member when the safety pull engages the body shield member.

9. The injector of claim 1, wherein the perimeter of the top circular plane surface is chamfered.

10. The injector of claim 1, wherein the body shield member has at least one bore, the cylindrical handle has at least one socket, and a fastener passes through the at least one bore of the body shield member to engage the at least one socket, the fastener preventing the handle from separating from the body shield member.

11. The injector of claim 1, wherein the high force spring requires approximately 150 grams to compress.

12. The injector of claim 1, wherein the low-force spring requires approximately 50 grams to compress.

13. The injector of claim 1, wherein the syringe barrel has a volume of approximately 0.3 cc.

14. The injector of claim 1, wherein the needle is a 30 gauge needle.

15. An injector for delivering a dose of a pharmaceutical comprising:
   (a) a body shield member for engaging a limb, comprising:
      a concave flange on a lower end of the body shield member; and a stop wall surrounding a orifice and having a top surface which controls the exposure depth of a needle;
(b) a cylindrical handle that travels along the central axis relative to the central pipe portion of the body shield member, comprising:
a top circular plane surface on an upper end of the handle;
an internal cavity that extends between an upper end and a lower end of the handle; and
a boss at the upper end of the handle;
(c) a syringe assembly having an upper end and a lower end, the upper end being disposed within the internal cavity of the handle against the top circular plane surface, the lower end disposed within the body shield member, the syringe assembly comprising:
an inner barrel with a push wall and at least one pin;
an outer sleeve surrounding the inner barrel, the outer sleeve having a helically curved slot mating with the at least one pin of the inner barrel, and having a flange on a lower end of the sleeve;
a plunger assembly having a push disc and a head;
a syringe barrel located between the plunger assembly head and the needle;
a torsion spring surrounding the outer sleeve that engages the handle boss and engages the flange of the outer sleeve; and
a low-force compression spring located between the inner barrel and a top surface of the concave flange, wherein the low-force compression spring biases the syringe assembly apart from the body shield member.

16. The injector of claim 15, wherein the body shield member includes a ridge to maintain a minimum distance between the outer sleeve and the concave flange.

17. The injector of claim 15, wherein the body shield member includes a retainer that surrounds the outer sleeve and attaches to the cylindrical handle, the retainer being used to maintain a minimum distance between the outer sleeve and the concave flange.

18. The injector of claim 15, wherein the inner barrel has a barbell shape, and the cylindrical handle includes two rails along which the inner barrel travels.

19. A method of delivering a dose of a pharmaceutical through an injector, the method comprising:
providing an injector of claim 1;
placing the body shield member against the patient's limb;
pressing the handle toward the limb, causing the syringe assembly to extend a needle for a specified penetration depth;
injecting a specified dosage into the patient for a predetermined period of time;
retracting the needle into the injector after a predetermined period of time;
locking the handle so that it cannot be pressed again and the needle cannot be re-exposed; and
removing the injector from the patient's limb.

20. The method of claim 19, further comprising removing a safety pull allowing the press handle to be pressed.

* * * * *